United States Patent
Kang et al.

(10) Patent No.: US 11,622,929 B2
(45) Date of Patent: Apr. 11, 2023

(54) LONG LASTING COSMETIC COMPOSITIONS

(71) Applicant: Living Proof, Inc., Boston, MA (US)

(72) Inventors: Soo-Young Kang, Bedford, MA (US); Sara A. Turner, Boston, MA (US); Ling-Fang Tseng, Boston, MA (US); Zhaoxia Ji, Natick, MA (US); Eric G. Spengler, Boston, MA (US)

(73) Assignee: Living Proof, Inc., Boston, MA (US)

( * ) Notice: Subject to any disclaimer, the term of this patent is extended or adjusted under 35 U.S.C. 154(b) by 0 days.

(21) Appl. No.: 15/451,897

(22) Filed: Mar. 7, 2017

(65) Prior Publication Data

US 2017/0258700 A1    Sep. 14, 2017

Related U.S. Application Data

(60) Provisional application No. 62/437,462, filed on Dec. 21, 2016, provisional application No. 62/305,275, filed on Mar. 8, 2016.

(51) Int. Cl.

| | | |
|---|---|---|
| *A61K 8/87* | (2006.01) | |
| *A61K 8/37* | (2006.01) | |
| *A61K 8/35* | (2006.01) | |
| *A61K 8/36* | (2006.01) | |
| *C08G 18/32* | (2006.01) | |
| *C08G 18/38* | (2006.01) | |
| *C08G 18/44* | (2006.01) | |
| *C08G 18/66* | (2006.01) | |
| *C08G 18/75* | (2006.01) | |
| *A61Q 5/06* | (2006.01) | |
| *A61K 8/04* | (2006.01) | |
| *C08G 18/10* | (2006.01) | |
| *C08G 18/22* | (2006.01) | |
| *C08G 18/08* | (2006.01) | |
| *C08G 18/34* | (2006.01) | |

(52) U.S. Cl.
CPC ............. *A61K 8/87* (2013.01); *A61K 8/04* (2013.01); *A61K 8/35* (2013.01); *A61K 8/361* (2013.01); *A61K 8/37* (2013.01); *A61Q 5/06* (2013.01); *C08G 18/0814* (2013.01); *C08G 18/0823* (2013.01); *C08G 18/10* (2013.01); *C08G 18/222* (2013.01); *C08G 18/3206* (2013.01); *C08G 18/348* (2013.01); *C08G 18/3821* (2013.01); *C08G 18/44* (2013.01); *C08G 18/664* (2013.01); *C08G 18/6659* (2013.01); *C08G 18/755* (2013.01); *C08G 18/758* (2013.01); *A61K 2800/412* (2013.01); *A61K 2800/413* (2013.01)

(58) Field of Classification Search
CPC ............. C08G 18/10; C08G 18/3206; C08G 18/348; C08G 18/3821; C08G 18/3275; C08G 18/0814; C08G 18/0823; C08G 18/222; C08G 18/44; C08G 18/664; C08G 18/6659; C08G 18/755; C08G 18/758; A61K 2800/412; A61K 2800/413; A61K 8/04; A61K 8/35; A61K 8/361; A61K 8/37; A61K 8/87; A61Q 5/06
See application file for complete search history.

(56) References Cited

U.S. PATENT DOCUMENTS

| | | |
|---|---|---|
| 3,104,424 A | 9/1963 | Immel |
| 3,262,686 A | 7/1966 | Kraus et al. |
| 3,803,063 A | 4/1974 | Krentz, Jr. |
| 4,071,614 A | 1/1978 | Grimm, III |
| 4,455,146 A | 6/1984 | Noda et al. |
| 4,950,542 A | 8/1990 | Barker |
| 5,110,852 A | 5/1992 | Gogolewski et al. |
| 5,281,654 A | 1/1994 | Eisenhart et al. |
| 5,290,543 A | 3/1994 | Ounanian et al. |
| 5,335,373 A | 8/1994 | Dresdner, Jr. et al. |
| 5,357,636 A | 10/1994 | Dresdner, Jr. et al. |
| 5,362,486 A | 11/1994 | Nandagiri et al. |
| 5,534,265 A | 7/1996 | Fowler et al. |
| 5,534,348 A | 7/1996 | Miller et al. |
| 5,540,853 A | 7/1996 | Trinh et al. |
| 5,626,840 A | 5/1997 | Thomaides et al. |
| 5,637,291 A | 6/1997 | Bara et al. |
| 5,643,581 A | 7/1997 | Mougin et al. |
| 5,720,961 A | 2/1998 | Fowler et al. |
| 5,733,572 A | 3/1998 | Unger et al. |
| 5,807,540 A | 9/1998 | Junino et al. |
| 5,833,967 A | 11/1998 | Ramin |
| 5,846,551 A | 12/1998 | DaCunha et al. |
| 5,849,310 A | 12/1998 | Trinh et al. |
| 5,891,463 A | 4/1999 | Bello et al. |
| 5,900,457 A | 5/1999 | Duan et al. |
| 5,912,299 A | 6/1999 | Tomko et al. |
| 5,914,117 A | 6/1999 | Lavaud |

(Continued)

FOREIGN PATENT DOCUMENTS

| | | |
|---|---|---|
| BR | PI0405064 A | 8/2005 |
| BR | 102013022835 A2 | 8/2015 |

(Continued)

OTHER PUBLICATIONS

Srivastava et al., Indian Application No. 148/DEL/2010. Bioreactor and Uses Thereof. Filed Jul. 29, 2011. 20 pages.

Teixeira et al., A case study of product engineering: Performance of microencapsulated perfumes on textile applications. AIChE Journal. Jun. 2011;58(6):1939-1950.

International Search Report and Written Opinion for Application No. PCT/US2017/021025, dated May 23, 2017.

Adina, Natpure Hollowbead. Adina Cosmetic Ingredients Ltd., retrieved online at: http://www.cosmeticingredients.co.uk/ingredient/natpure-hollowbead. 2 pages, (2015).

(Continued)

*Primary Examiner* — Anna R Falkowitz
(74) *Attorney, Agent, or Firm* — McCarter & English, LLP; Michael J. DeGrazia; Xiaoyuan Ding

(57) ABSTRACT

Provided herein long lasting cosmetic compositions and markers for selecting the same.

13 Claims, 15 Drawing Sheets

(56) References Cited

U.S. PATENT DOCUMENTS

| | | |
|---|---|---|
| 5,932,194 A | 8/1999 | Plessix et al. |
| 5,932,200 A | 8/1999 | Reich et al. |
| 5,993,972 A | 11/1999 | Reich et al. |
| 6,007,793 A | 12/1999 | Bhatt et al. |
| 6,084,051 A | 7/2000 | Blum et al. |
| 6,086,903 A | 7/2000 | Trinh et al. |
| 6,106,813 A | 8/2000 | Mondet et al. |
| 6,126,930 A | 10/2000 | Dubois et al. |
| 6,130,309 A | 10/2000 | Reich et al. |
| 6,132,704 A | 10/2000 | Bhatt et al. |
| 6,153,179 A | 11/2000 | Blankenburg et al. |
| 6,156,325 A | 12/2000 | Farer et al. |
| 6,221,344 B1 | 4/2001 | Ramin et al. |
| 6,238,651 B1 | 5/2001 | Bara |
| 6,254,876 B1 | 7/2001 | de la Poterie et al. |
| 6,277,386 B1 | 8/2001 | Kim et al. |
| 6,277,401 B1 | 8/2001 | Bello et al. |
| 6,291,580 B1 | 9/2001 | Kukkala et al. |
| 6,298,558 B1 | 10/2001 | Tseng et al. |
| 6,319,959 B1 | 11/2001 | Mougin et al. |
| 6,326,013 B1 | 12/2001 | Lemann et al. |
| 6,346,234 B1 | 2/2002 | Rollat et al. |
| 6,361,782 B1 | 3/2002 | Chevalier et al. |
| 6,365,697 B1 | 4/2002 | Kim et al. |
| 6,372,876 B1 | 4/2002 | Kim et al. |
| 6,403,070 B1 | 6/2002 | Pataut et al. |
| 6,403,107 B1 | 6/2002 | Lemann |
| 6,403,542 B1 | 6/2002 | Maurin et al. |
| 6,409,998 B1 | 6/2002 | Candau et al. |
| 6,433,073 B1 | 8/2002 | Kantner et al. |
| 6,465,534 B2 | 10/2002 | Fukuzawa et al. |
| 6,469,227 B1 | 10/2002 | Cooke et al. |
| 6,485,950 B1 | 11/2002 | Kumar et al. |
| 6,517,821 B1 | 2/2003 | Rollat et al. |
| 6,520,186 B2 | 2/2003 | Rollat et al. |
| 6,524,564 B1 | 2/2003 | Kim et al. |
| 6,524,597 B2 | 2/2003 | Kashimoto |
| 6,531,118 B1 | 3/2003 | Gonzalez et al. |
| 6,555,096 B2 | 4/2003 | Carrion et al. |
| 6,576,024 B1 | 6/2003 | Lang et al. |
| 6,576,702 B2 | 6/2003 | Anderle et al. |
| 6,579,517 B1 | 6/2003 | Kim et al. |
| 6,592,881 B1 | 7/2003 | Fukuda et al. |
| 6,613,314 B1 | 9/2003 | Rollat et al. |
| 6,635,262 B2 | 10/2003 | Jourdan et al. |
| 6,641,804 B1 | 11/2003 | Ohta et al. |
| 6,682,748 B1 | 1/2004 | De La Poterie et al. |
| 6,689,345 B2 | 2/2004 | Jager Lezer |
| 6,692,729 B1 | 2/2004 | Asaoka et al. |
| 6,719,959 B1 | 4/2004 | Gonzalez et al. |
| 6,730,289 B2 | 5/2004 | Khoshdel |
| 6,750,291 B2 | 6/2004 | Kim et al. |
| 6,800,276 B2 | 10/2004 | Kim et al. |
| 6,830,758 B2 | 12/2004 | Nichols et al. |
| 6,884,853 B1 | 4/2005 | Asaoka et al. |
| 6,897,281 B2 | 5/2005 | Lubnin et al. |
| 6,927,254 B2 | 8/2005 | Melchiors et al. |
| 7,019,061 B2 | 3/2006 | Meffert et al. |
| 7,098,178 B2 | 8/2006 | Gerke et al. |
| 7,101,954 B2 | 9/2006 | Zofchak et al. |
| 7,160,553 B2 | 1/2007 | Gibbins et al. |
| 7,326,256 B2 | 2/2008 | Cottard et al. |
| 7,348,299 B2 | 3/2008 | Keenan et al. |
| 7,445,770 B2 | 11/2008 | Berezkin et al. |
| 7,452,525 B1 | 11/2008 | Berezkin et al. |
| 7,481,996 B2 | 1/2009 | Ishii et al. |
| 7,659,233 B2 | 2/2010 | Hurley et al. |
| 7,700,082 B2 | 4/2010 | Mallo et al. |
| 7,740,832 B1 | 6/2010 | Rollat-Corvol et al. |
| 7,744,911 B2 | 6/2010 | Pechko et al. |
| RE41,615 E | 8/2010 | Kim et al. |
| 7,829,099 B2 | 11/2010 | Woeller et al. |
| 7,907,346 B2 | 3/2011 | Swarup et al. |
| 7,914,775 B2 | 3/2011 | Cottard et al. |
| 7,959,903 B2 | 6/2011 | Candau et al. |
| 7,972,589 B2 | 7/2011 | Leighton et al. |
| 7,998,465 B2 | 8/2011 | De La Poterie et al. |
| 8,067,355 B2 | 11/2011 | Smets et al. |
| 8,258,093 B2 | 9/2012 | Van Dyke |
| 8,343,523 B2 | 1/2013 | Toreki et al. |
| 8,449,871 B2 | 5/2013 | Mougin et al. |
| 8,497,338 B2 | 7/2013 | Bai et al. |
| 8,623,388 B2 | 1/2014 | Rajaiah et al. |
| 8,629,213 B2 | 1/2014 | Hidalgo et al. |
| 8,679,050 B2 | 3/2014 | Nakamura |
| 8,679,465 B2 | 3/2014 | Malnou et al. |
| 8,734,772 B1 | 5/2014 | Zhou et al. |
| 8,741,333 B2 | 6/2014 | Zhang et al. |
| 8,784,854 B2 | 7/2014 | Choi et al. |
| 8,871,817 B2 | 10/2014 | Turk et al. |
| 8,882,902 B2 | 11/2014 | Suzuki et al. |
| 8,895,040 B2 | 11/2014 | Vondruska et al. |
| 8,956,160 B2 | 2/2015 | Willison et al. |
| 8,956,162 B2 | 2/2015 | De Vreese et al. |
| 9,016,221 B2 | 4/2015 | Brennan et al. |
| RE45,538 E | 6/2015 | Smets et al. |
| 9,079,152 B2 | 7/2015 | Markus et al. |
| 9,101,143 B2 | 8/2015 | Markus et al. |
| 9,102,783 B2 | 8/2015 | Yagi et al. |
| 9,175,125 B2 | 11/2015 | Turk et al. |
| 9,295,632 B1 | 3/2016 | Benn et al. |
| 9,340,650 B2 | 5/2016 | Wagner et al. |
| 9,393,218 B2 | 7/2016 | Zurdo Schroeder et al. |
| 2001/0031280 A1 | 10/2001 | Ferrari et al. |
| 2002/0028875 A1 | 3/2002 | Anderle et al. |
| 2002/0034480 A1 | 3/2002 | Grimm et al. |
| 2002/0034486 A1 | 3/2002 | Midha et al. |
| 2002/0102222 A1 | 8/2002 | Carrion et al. |
| 2002/0107314 A1 | 8/2002 | Pinzon et al. |
| 2002/0114773 A1 | 8/2002 | Kanji et al. |
| 2002/0155962 A1 | 10/2002 | Cincotta et al. |
| 2002/0164297 A1 | 11/2002 | Ferrari et al. |
| 2002/0192273 A1 | 12/2002 | Buseman et al. |
| 2003/0026815 A1 | 2/2003 | Scott et al. |
| 2003/0064086 A1 | 4/2003 | Carrion et al. |
| 2003/0082126 A9 | 5/2003 | Pinzon et al. |
| 2003/0086886 A1 | 5/2003 | Midha |
| 2003/0086896 A1 | 5/2003 | Midha et al. |
| 2003/0099694 A1 | 5/2003 | Cevc et al. |
| 2003/0125427 A9 | 7/2003 | Pinzon et al. |
| 2003/0185780 A1 | 10/2003 | Ferrari et al. |
| 2003/0190345 A1 | 10/2003 | Cordes et al. |
| 2003/0191154 A1 | 10/2003 | Kalafsky et al. |
| 2003/0198659 A1 | 10/2003 | Hoffmann et al. |
| 2003/0203991 A1 | 10/2003 | Schottman et al. |
| 2004/0001798 A1 | 1/2004 | Perron et al. |
| 2004/0057914 A1 | 3/2004 | Bonda et al. |
| 2004/0071757 A1 | 4/2004 | Rolf |
| 2004/0086482 A1 | 5/2004 | Zofchak et al. |
| 2004/0120915 A1 | 6/2004 | Yang et al. |
| 2004/0131573 A1 | 7/2004 | Tang |
| 2004/0137028 A1 | 7/2004 | de la Poterie |
| 2004/0156804 A1 | 8/2004 | Poterie et al. |
| 2004/0166076 A1 | 8/2004 | Ferrari et al. |
| 2004/0166133 A1 | 8/2004 | Cavazzuti et al. |
| 2004/0176487 A1 | 9/2004 | Svedberg et al. |
| 2004/0186259 A1 | 9/2004 | Brehm et al. |
| 2004/0197286 A1 | 10/2004 | Robert et al. |
| 2004/0223987 A1 | 11/2004 | Ferrari |
| 2004/0228886 A1 | 11/2004 | Ding et al. |
| 2004/0247549 A1 | 12/2004 | Lu et al. |
| 2005/0008667 A1 | 1/2005 | Liechty et al. |
| 2005/0014674 A1 | 1/2005 | Liechty et al. |
| 2005/0043209 A1 | 2/2005 | Schmiedel et al. |
| 2005/0089540 A1 | 4/2005 | Uchiyama et al. |
| 2005/0118126 A1 | 6/2005 | Rollat et al. |
| 2005/0148753 A1 | 7/2005 | Nguyen-Kim et al. |
| 2005/0163741 A1 | 7/2005 | Zech |
| 2005/0169873 A1 | 8/2005 | Rollat et al. |
| 2005/0169874 A1 | 8/2005 | Zofchak et al. |
| 2005/0209428 A1 | 9/2005 | Tamareselvy |
| 2005/0220740 A1 | 10/2005 | Dumousseaux |
| 2005/0220741 A1 | 10/2005 | Dumousseaux |
| 2005/0249691 A1 | 11/2005 | Monks et al. |

(56) References Cited

U.S. PATENT DOCUMENTS

| | | |
|---|---|---|
| 2005/0276831 A1 | 12/2005 | Dihora et al. |
| 2005/0287100 A1 | 12/2005 | Lebre |
| 2005/0287103 A1 | 12/2005 | Filippi et al. |
| 2005/0287182 A1 | 12/2005 | Monks et al. |
| 2005/0287183 A1 | 12/2005 | Lebre |
| 2006/0045890 A1 | 3/2006 | Gonzalez et al. |
| 2006/0045893 A1 | 3/2006 | Yu et al. |
| 2006/0051311 A1 | 3/2006 | Walter et al. |
| 2006/0073106 A1 | 4/2006 | Berg-Schultz et al. |
| 2006/0078519 A1 | 4/2006 | Lion et al. |
| 2006/0083762 A1 | 4/2006 | Brun et al. |
| 2006/0099550 A1 | 5/2006 | Faasse et al. |
| 2006/0120983 A1 | 6/2006 | Blin et al. |
| 2006/0134049 A1 | 6/2006 | Keenan et al. |
| 2006/0171984 A1 | 8/2006 | Cromack et al. |
| 2006/0193789 A1 | 8/2006 | Famarkin et al. |
| 2006/0216250 A1 | 9/2006 | Schultz et al. |
| 2006/0233728 A1 | 10/2006 | Sagawa et al. |
| 2006/0281650 A1 | 12/2006 | Keenan et al. |
| 2006/0287219 A1 | 12/2006 | Dykstra et al. |
| 2007/0032605 A1 | 2/2007 | Harashina |
| 2007/0105977 A1 | 5/2007 | Gabriel et al. |
| 2007/0167565 A1 | 7/2007 | Rische et al. |
| 2007/0183992 A1 | 8/2007 | Dumousseaux et al. |
| 2007/0183997 A9 | 8/2007 | Lebre et al. |
| 2007/0189980 A1 | 8/2007 | Zhang et al. |
| 2007/0197704 A1 | 8/2007 | Walter et al. |
| 2007/0207222 A1 | 9/2007 | Yu et al. |
| 2007/0251026 A1 | 11/2007 | Lalleman et al. |
| 2008/0044373 A1 | 2/2008 | Ilekti et al. |
| 2008/0044445 A1 | 2/2008 | Rubin |
| 2008/0045985 A1 | 2/2008 | Gurtner et al. |
| 2008/0138368 A1 | 6/2008 | Lezer |
| 2008/0175875 A1 | 7/2008 | Sunkara |
| 2008/0254074 A1 | 10/2008 | Dussaud et al. |
| 2009/0049623 A1 | 2/2009 | Brown et al. |
| 2009/0056734 A1 | 3/2009 | Bacon |
| 2009/0061004 A1 | 3/2009 | Birkel et al. |
| 2009/0105195 A1 | 4/2009 | O'Brien |
| 2009/0112141 A1 | 4/2009 | Derr |
| 2009/0175928 A1 | 7/2009 | Maier et al. |
| 2009/0196842 A1 | 8/2009 | Zech et al. |
| 2009/0257960 A1 | 10/2009 | Kim et al. |
| 2009/0263338 A1 | 10/2009 | Rolland et al. |
| 2009/0285866 A1 | 11/2009 | Afriat et al. |
| 2010/0003198 A1 | 1/2010 | Stolmeier et al. |
| 2010/0233146 A1 | 9/2010 | McDaniel |
| 2010/0260687 A1 | 10/2010 | Yu et al. |
| 2010/0261629 A1 | 10/2010 | Smets et al. |
| 2010/0297036 A1 | 11/2010 | Feuillette |
| 2010/0325812 A1 | 12/2010 | Panandiker et al. |
| 2010/0325813 A1 | 12/2010 | Dykstra et al. |
| 2011/0010817 A1 | 1/2011 | Theberge et al. |
| 2011/0027211 A1* | 2/2011 | Viala .............. A61K 8/87 424/70.17 |
| 2011/0046286 A1 | 2/2011 | Lubnin et al. |
| 2011/0117042 A1 | 5/2011 | Viala et al. |
| 2011/0200927 A1 | 8/2011 | Jung et al. |
| 2011/0229430 A1 | 9/2011 | Hawkins et al. |
| 2011/0230474 A1 | 9/2011 | Grigorian et al. |
| 2011/0256311 A1 | 10/2011 | Mattos, Jr. |
| 2011/0272320 A1 | 11/2011 | Mwattari et al. |
| 2011/0274633 A1 | 11/2011 | Vu et al. |
| 2012/0255574 A1 | 10/2012 | Flohr et al. |
| 2013/0084256 A1 | 4/2013 | Li et al. |
| 2013/0161349 A1 | 6/2013 | Pfeiffenberger |
| 2013/0196849 A1 | 8/2013 | Combs et al. |
| 2013/0239344 A1 | 9/2013 | Stolarz, Jr. et al. |
| 2013/0239874 A1 | 9/2013 | Smith et al. |
| 2013/0261255 A1 | 10/2013 | Deyrail et al. |
| 2014/0010776 A1* | 1/2014 | Viala .............. A61K 8/87 424/70.11 |
| 2014/0044657 A1 | 2/2014 | Kelly et al. |
| 2014/0066496 A1 | 3/2014 | Gunari et al. |
| 2014/0086864 A1 | 3/2014 | Ishimori et al. |
| 2014/0105846 A1 | 4/2014 | Viala et al. |
| 2014/0142191 A1 | 5/2014 | De La Zerda et al. |
| 2014/0147396 A1 | 5/2014 | Sertchook et al. |
| 2014/0170327 A1 | 6/2014 | Dombrowski et al. |
| 2014/0219927 A1 | 8/2014 | Belluscio et al. |
| 2014/0248270 A1 | 9/2014 | Yu et al. |
| 2014/0248340 A1 | 9/2014 | Schwarzentruber et al. |
| 2014/0350269 A1 | 11/2014 | Eiji Borges Sato |
| 2015/0004117 A1 | 1/2015 | Tan et al. |
| 2015/0007849 A1 | 1/2015 | Cajan et al. |
| 2015/0071978 A1 | 3/2015 | Chang |
| 2015/0118331 A1 | 4/2015 | Boam et al. |
| 2015/0119497 A1 | 4/2015 | Matsui et al. |
| 2015/0190450 A1 | 7/2015 | Chang |
| 2015/0238406 A1 | 8/2015 | Pohlmann et al. |
| 2015/0283041 A1 | 10/2015 | Benn et al. |
| 2015/0342845 A1 | 12/2015 | Hwang et al. |
| 2015/0344622 A1 | 12/2015 | Mukerjee et al. |
| 2016/0001099 A1 | 1/2016 | Castro et al. |
| 2016/0058678 A1 | 3/2016 | Smets et al. |
| 2016/0074311 A1 | 3/2016 | Massey-Brooker et al. |
| 2016/0143836 A1 | 5/2016 | Hayes et al. |
| 2016/0175233 A1 | 6/2016 | Benn |
| 2016/0175238 A1 | 6/2016 | Shin et al. |
| 2016/0184195 A1 | 6/2016 | Tan et al. |
| 2016/0220475 A1 | 8/2016 | Scherner et al. |
| 2017/0216188 A1 | 8/2017 | Bermudez Agudelo et al. |
| 2018/0000699 A1 | 1/2018 | Trahan |
| 2019/0076347 A1 | 3/2019 | Kang et al. |
| 2019/0076348 A1 | 3/2019 | Kang et al. |
| 2019/0151221 A1 | 5/2019 | Kang et al. |
| 2019/0359786 A1 | 11/2019 | Trahan et al. |
| 2021/0212920 A1 | 7/2021 | Kang et al. |
| 2022/0105021 A1 | 4/2022 | Kang et al. |

FOREIGN PATENT DOCUMENTS

| | | |
|---|---|---|
| CN | 1236783 A | 12/1999 |
| CN | 1370063 A | 9/2002 |
| CN | 1370185 A | 9/2002 |
| CN | 1413102 A | 4/2003 |
| CN | 1476320 A | 2/2004 |
| CN | 1487962 A | 4/2004 |
| CN | 1650840 A | 8/2005 |
| CN | 1708524 A | 12/2005 |
| CN | 1775826 A | 5/2006 |
| CN | 101124256 A | 2/2008 |
| CN | 101130082 A | 2/2008 |
| CN | 101361701 A | 2/2009 |
| CN | 101484130 A | 7/2009 |
| CN | 101980691 A | 2/2011 |
| CN | 102015803 A | 4/2011 |
| CN | 102575051 A | 7/2012 |
| CN | 102895164 A | 1/2013 |
| CN | 103314025 A | 9/2013 |
| CN | 104188877 A | 12/2014 |
| CN | 105213260 A | 1/2016 |
| CN | 105561841 A | 5/2016 |
| CN | 105764484 A | 7/2016 |
| CN | 109071750 A | 12/2018 |
| DE | 102015204154 A1 | 9/2016 |
| EP | 727981 A1 | 8/1996 |
| EP | 789550 A1 | 8/1997 |
| EP | 923927 A1 | 6/1999 |
| EP | 1058560 A1 | 12/2000 |
| EP | 1082953 A1 | 3/2001 |
| EP | 1090632 A1 | 4/2001 |
| EP | 1090633 A1 | 4/2001 |
| EP | 1092419 A1 | 4/2001 |
| EP | 1155676 A2 | 11/2001 |
| EP | 1161937 A2 | 12/2001 |
| EP | 1216690 A2 | 6/2002 |
| EP | 1218430 A1 | 7/2002 |
| EP | 1289363 A3 | 3/2003 |
| EP | 1417886 A1 | 5/2004 |
| EP | 1419759 A2 | 5/2004 |
| EP | 1481661 A2 | 12/2004 |
| EP | 1491179 A2 | 12/2004 |
| EP | 1579841 A1 | 9/2005 |

(56) References Cited

FOREIGN PATENT DOCUMENTS

| | | |
|---|---|---|
| EP | 1579849 A1 | 9/2005 |
| EP | 1598046 A1 | 11/2005 |
| EP | 1604634 A1 | 12/2005 |
| EP | 1707182 A1 | 10/2006 |
| EP | 1707183 A1 | 10/2006 |
| EP | 1773906 A1 | 4/2007 |
| EP | 1800671 A1 | 6/2007 |
| EP | 1903065 A2 | 3/2008 |
| EP | 2209472 A1 | 7/2010 |
| EP | 2271304 A1 | 1/2011 |
| EP | 2391424 A2 | 12/2011 |
| EP | 2591772 A1 | 5/2013 |
| EP | 2611466 A2 | 7/2013 |
| EP | 2726067 A1 | 5/2014 |
| EP | 2858630 A1 | 4/2015 |
| EP | 2859794 A1 | 4/2015 |
| EP | 2867298 A1 | 5/2015 |
| EP | 2925296 A1 | 10/2015 |
| EP | 2995217 A1 | 3/2016 |
| EP | 3020454 A1 | 5/2016 |
| FR | 2801209 A1 | 5/2001 |
| FR | 2815350 A1 | 4/2002 |
| FR | 2816834 A1 | 5/2002 |
| FR | 2835529 A1 | 8/2003 |
| FR | 2892931 A1 | 5/2007 |
| FR | 2902655 A1 | 12/2007 |
| FR | 2940093 A1 | 6/2010 |
| FR | 2957347 A1 | 9/2011 |
| FR | 2967062 A1 | 5/2012 |
| JP | H06362 A | 1/1994 |
| JP | H1080973 A | 3/1998 |
| JP | 2002-020451 A | 1/2002 |
| JP | 2004-256694 A | 9/2004 |
| JP | 2006290845 A | 10/2006 |
| JP | 2010132568 A | 6/2010 |
| JP | 2011173851 A | 9/2011 |
| JP | 2011-246352 A | 12/2011 |
| JP | 2012-057110 A | 3/2012 |
| JP | 2016094362 A | 5/2016 |
| KR | 20080064230 A | 7/2008 |
| KR | 20090058294 A | 6/2009 |
| KR | 20090081582 A | 7/2009 |
| KR | 20110062277 A | 6/2011 |
| KR | 20140078356 A | 6/2014 |
| KR | 20140093349 A | 7/2014 |
| KR | 20140121154 A | 10/2014 |
| WO | 1989007959 A1 | 9/1989 |
| WO | 1991001970 A2 | 2/1991 |
| WO | 199413354 A1 | 6/1994 |
| WO | 199813025 A1 | 4/1998 |
| WO | 199826751 A1 | 6/1998 |
| WO | 199826756 A1 | 6/1998 |
| WO | 199912519 A1 | 3/1999 |
| WO | 199955288 A1 | 11/1999 |
| WO | 199955290 A1 | 11/1999 |
| WO | 199955291 A1 | 11/1999 |
| WO | 199955292 A1 | 11/1999 |
| WO | 199956708 A1 | 11/1999 |
| WO | 200014091 A1 | 3/2000 |
| WO | 2000016752 A2 | 3/2000 |
| WO | 2000018367 A1 | 4/2000 |
| WO | 2000027350 A1 | 5/2000 |
| WO | 2000/40628 A1 | 7/2000 |
| WO | 2001003652 A2 | 1/2001 |
| WO | 2001024768 A2 | 4/2001 |
| WO | 2001068037 A2 | 9/2001 |
| WO | 2001078691 A1 | 10/2001 |
| WO | 2001087065 A1 | 11/2001 |
| WO | 2001094438 A1 | 12/2001 |
| WO | 2002007699 A1 | 1/2002 |
| WO | 2002039961 A1 | 5/2002 |
| WO | 2002039964 A1 | 5/2002 |
| WO | 2002043490 A1 | 6/2002 |
| WO | 2002043491 A1 | 6/2002 |
| WO | 2002045663 A1 | 6/2002 |
| WO | 2002047620 A2 | 6/2002 |
| WO | 2002047624 A1 | 6/2002 |
| WO | 2002047626 A1 | 6/2002 |
| WO | 2002047628 A1 | 6/2002 |
| WO | 2002047657 A2 | 6/2002 |
| WO | 2002047658 A2 | 6/2002 |
| WO | 2002054997 A1 | 7/2002 |
| WO | 2002055034 A2 | 7/2002 |
| WO | 2002072045 A2 | 9/2002 |
| WO | 2003/028678 A1 | 4/2003 |
| WO | 2003094870 A1 | 11/2003 |
| WO | 2004110401 A2 | 12/2004 |
| WO | 2005014777 A2 | 2/2005 |
| WO | 2005017134 A2 | 2/2005 |
| WO | 2005092963 A1 | 10/2005 |
| WO | 2006015718 A1 | 2/2006 |
| WO | 2006062740 A2 | 6/2006 |
| WO | 2006/127883 A2 | 11/2006 |
| WO | 2006131403 A1 | 12/2006 |
| WO | 2007057059 A1 | 5/2007 |
| WO | 2007070643 A2 | 6/2007 |
| WO | 2007071886 A2 | 6/2007 |
| WO | 2007077029 A1 | 7/2007 |
| WO | 2007145395 A1 | 12/2007 |
| WO | 2008006677 A1 | 1/2008 |
| WO | 2008006687 A1 | 1/2008 |
| WO | 2008024408 A2 | 2/2008 |
| WO | 2008125406 A2 | 10/2008 |
| WO | 2008133982 A2 | 11/2008 |
| WO | 2008148809 A1 | 12/2008 |
| WO | 2009014347 A2 | 1/2009 |
| WO | 2009053594 A2 | 4/2009 |
| WO | 2010003138 A1 | 1/2010 |
| WO | 2010006442 A1 | 1/2010 |
| WO | 2010037402 A1 | 4/2010 |
| WO | 2010076483 A1 | 7/2010 |
| WO | 2010079468 A2 | 7/2010 |
| WO | 2010086754 A2 | 8/2010 |
| WO | 2010129299 A2 | 11/2010 |
| WO | 2011016140 A1 | 2/2011 |
| WO | 2011016531 A1 | 2/2011 |
| WO | 2011075556 A1 | 6/2011 |
| WO | 2011089709 A1 | 7/2011 |
| WO | 2011/126978 A1 | 10/2011 |
| WO | 2011140330 A2 | 11/2011 |
| WO | 2012037445 A2 | 3/2012 |
| WO | 2012063947 A1 | 5/2012 |
| WO | 2012087510 A1 | 6/2012 |
| WO | 2012117013 A1 | 9/2012 |
| WO | 2012121704 A1 | 9/2012 |
| WO | 2012168102 A2 | 12/2012 |
| WO | 2013/064596 A1 | 5/2013 |
| WO | 2013068478 A1 | 5/2013 |
| WO | 2013071079 A1 | 5/2013 |
| WO | 2013149323 A1 | 10/2013 |
| WO | 2013/165424 A1 | 11/2013 |
| WO | 2014001574 A1 | 1/2014 |
| WO | 2014001985 A1 | 1/2014 |
| WO | 2014014139 A1 | 1/2014 |
| WO | 2014/111579 A2 | 7/2014 |
| WO | 2014105676 A1 | 7/2014 |
| WO | 2014176515 A2 | 10/2014 |
| WO | 2014/210117 A1 | 12/2014 |
| WO | 2015020060 A1 | 2/2015 |
| WO | 2015028417 A1 | 3/2015 |
| WO | 2015028418 A1 | 3/2015 |
| WO | 2015028421 A1 | 3/2015 |
| WO | 2015028424 A1 | 3/2015 |
| WO | 2015051139 A1 | 4/2015 |
| WO | 2015188335 A1 | 12/2015 |
| WO | 2016016315 A1 | 2/2016 |
| WO | 2016058958 A1 | 4/2016 |
| WO | 2016069396 A2 | 5/2016 |
| WO | 2016074683 A1 | 5/2016 |
| WO | 2016087948 A2 | 6/2016 |
| WO | 2016096928 A1 | 6/2016 |
| WO | 2016100885 A1 | 6/2016 |

(56) References Cited

FOREIGN PATENT DOCUMENTS

| WO | 2016115257 A2 | 7/2016 |
|---|---|---|
| WO | 2016138249 A1 | 9/2016 |
| WO | 2017/155906 A1 | 9/2017 |

OTHER PUBLICATIONS

AkzoNobel, Product Specification for Expancel Microspheres, www.expancel.com, 2 pages, (2011).
Araujo et al., Techniques for reducing residual monomer content in polymers: a review. Polymer Engineering and Science. 64 pages, Jul. 1, 2002.
Lochhead et al., Polymers in Cosmetics: Recent Advances. From film-formers to rheology modifiers, polymers serve various functions. Retrieved online at: https://www.happi.com/contents/view_features/2005-11-15/polymers-in-cosmetics-recent-advances. 12 pages, Nov. 15, 2005.
Xu et al., Synthesis and Characterization of Cationic Waterborne Polyurethane based Polycarbonate Polyol. China Leather. Nov. 2011;40(21):1-14.
Yao et al., Application of bionic technology in textiles. Textile Dyeing and Finishing Journal. Dec. 2013;35(12):29-33.
Zhang et al., Working Manual of Large Scale Poultry Farm Laboratory. Golden Shield Publishing House p. 138, Oct. 2013.
Chinese Office Action for Application No. 201880058933.2, dated Aug. 4, 2021, 26 pages.
U.S. Appl. No. 16/348,644, filed May 9, 2019, 2019-0359786, Abandoned.
U.S. Appl. No. 16/128,620, filed Sep. 12, 2018, U.S. Pat. No. 10,987,300, Issued.
U.S. Appl. No. 17/231,587, filed Apr. 15, 2021, Abandoned.
U.S. Appl. No. 17/530,662, filed Nov. 19, 2021, Pending.
U.S. Appl. No. 16/128,622, filed Sep. 12, 2018, U.S. Pat. No. 10,842,729, Issued.
U.S. Appl. No. 17/071,198, filed Oct. 15, 2020, Abandoned.
U.S. Appl. No. 17/326,605, filed May 21, 2021, 2022-0105021, Published.
U.S. Appl. No. 16/195,584, filed Sep. 19, 2018, 2019-0151221, Published.
U.S. Appl. No. 17/050,803, filed Oct. 26, 2020, 2021-0212920, Published.

* cited by examiner

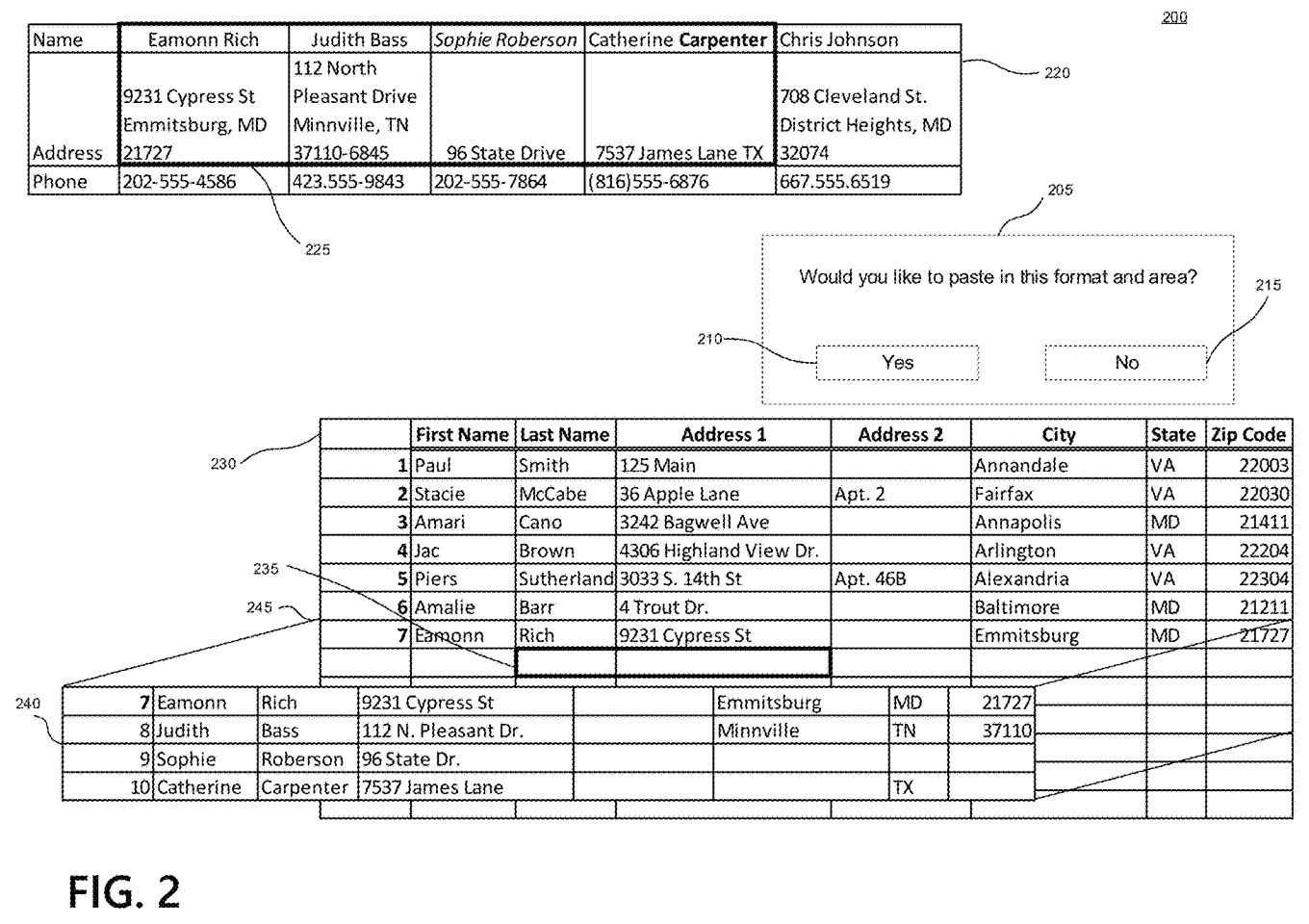

| Name | Eamonn Rich | Judith Bass | Sophie Roberson | Catherine Carpenter | Chris Johnson |
|---|---|---|---|---|---|
| Address | 9231 Cypress St Emmitsburg, MD 21727 | 112 North Pleasant Drive Minnville, TN 37110-6845 | 96 State Drive | 7537 James Lane TX | 708 Cleveland St. District Heights, MD 32074 |
| Phone | 202-555-4586 | 423-555-9843 | 202-555-7864 | (816)555-6876 | 667.555.6519 |

Would you like to paste in this format and area?

[ Yes ]   [ No ]

| | First Name | Last Name | Address 1 | Address 2 | City | State | Zip Code |
|---|---|---|---|---|---|---|---|
| 1 | Paul | Smith | 125 Main | | Annandale | VA | 22003 |
| 2 | Stacie | McCabe | 36 Apple Lane | Apt. 2 | Fairfax | VA | 22030 |
| 3 | Amari | Cano | 3242 Bagwell Ave | | Annapolis | MD | 21411 |
| 4 | Jac | Brown | 4306 Highland View Dr. | | Arlington | VA | 22204 |
| 5 | Piers | Sutherland | 3033 S. 14th St | Apt. 46B | Alexandria | VA | 22304 |
| 6 | Amalie | Barr | 4 Trout Dr. | | Baltimore | MD | 21211 |
| 7 | Eamonn | Rich | 9231 Cypress St | | Emmitsburg | MD | 21727 |
| | | | | Emmitsburg | MD | | 21727 |
| | | | | Minnville | TN | | 37110 |
| | | | | | TX | | |
| 7 | Eamonn | Rich | 9231 Cypress St | | | | |
| 8 | Judith | Bass | 112 N. Pleasant Dr. | | | | |
| 9 | Sophie | Roberson | 96 State Dr. | | | | |
| 10 | Catherine | Carpenter | 7537 James Lane | | | | |

FIG. 2

PVP/VA635    PU 162

Initial     After controlled humidity

Initial      After controlled humidity

Initial    After controlled humidity

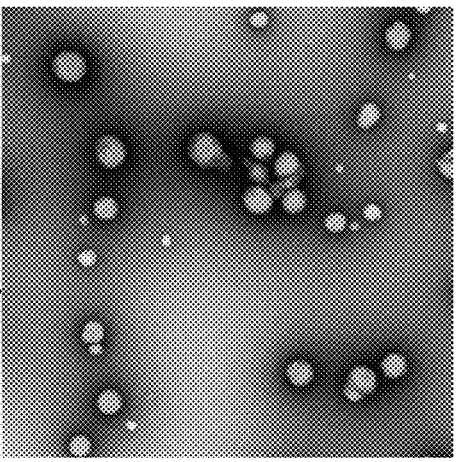
FIG. 13A LP PU 281
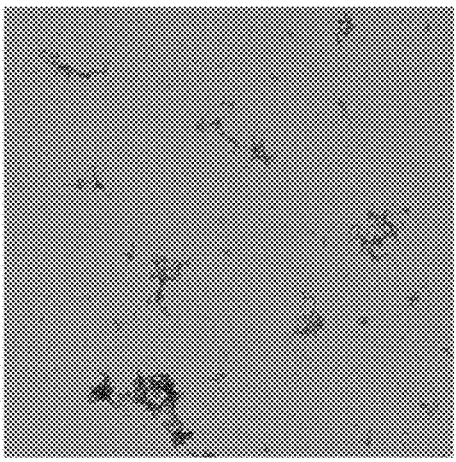
FIG. 13C DynamX H₂O
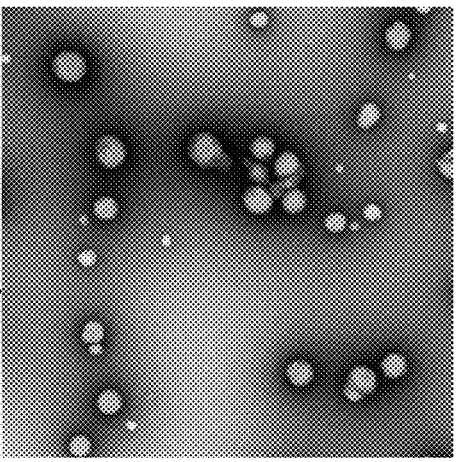
FIG. 13E Baycusan C1010
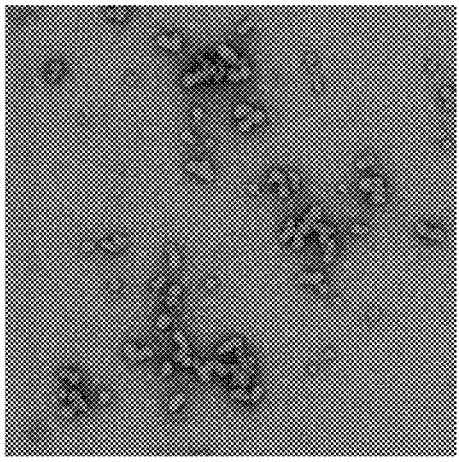
FIG. 13B
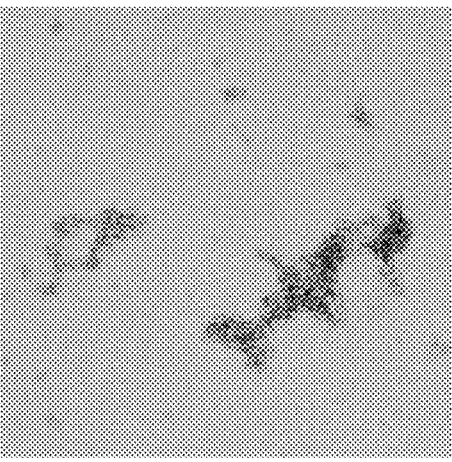
FIG. 13D
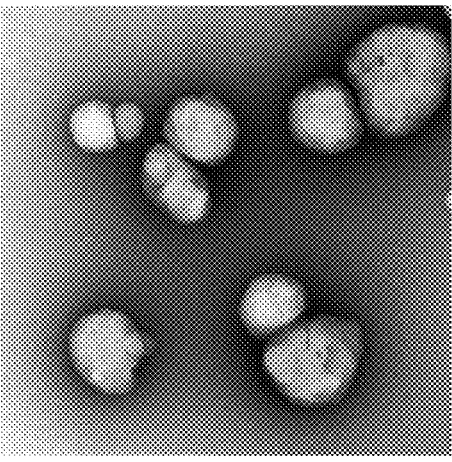
FIG. 13F

LONG LASTING COSMETIC COMPOSITIONS

REFERENCE TO RELATED APPLICATIONS

This application claims priority to U.S. Provisional Application No. 62/305,275, filed, Mar. 8, 2016 and U.S. Provisional Application No. 62/437,462, filed Dec. 21, 2016, the contents of each of which are incorporated herein by reference.

BACKGROUND

Polyurethanes and polyurethane-ureas are a well-known class of synthetic polymers with broad utility in multiple industries. This versatility is derived from the ability to prepare polyurethanes from a large and diverse set of potential monomers. These diverse monomer options allow the realization of an equally diverse set of physical properties. Hence, the resulting polyurethanes can be in many different forms including e.g., soft foams, elastomers, adhesive films, or hard plastics, and can be used in many different types of products including bedding, foot wear, adhesives, and automobile parts.

Among these many forms of polyurethanes, waterborne polyurethanes (WBPUs) and polyurethane-ureas (WBPU-Us) have been used as film forming agents in commercially available personal care products. When used as hair fixatives, these film forming polymers provide style-holding benefits. One such commercial product is Luviset® P.U.R. (BASF), which includes polyurethane-1, which is a copolymer consisting of isophthalic acid, adipic acid, hexylene glycol, neopentyl glycol, dimethylolpropanoic acid, and isophorone diisocyanate monomers (see SOFW Journal, Volume 126, Issue 11, Pages 26, 28, 30-32, 34, 2000). DynamX® and DynamX® $H_2O$ (AkzoNobel) include a Polyurethane-14 AMP-acrylate copolymer. Polyurethane-14 is a copolymer of polypropolene glycol, dimethylolpropanoic acid, a rigid diol, an amine-terminated polyether, and isophorone diisocyanate monomers (see Cosmetics & Toiletries magazine, Vol. 118, No. 1, p. 49-56, January 2003). Avalure® UR 405 (Lubrizol) includes polyurethane-2, which is a copolymer of hexanedioic acid, 2,2-dimethyl-1, 3-propanediol, 1,1'-methylenebis[4-isocyanatobenzene], 2-methyl-2,4-pentanediol, and 2,2-dimethylpropanoic acid. Baycusan® 1004 (Polyurethane-35, which is a copolymer of adipic acid, 1-6 HDI, NPG, dicyclohe xylmethane diisocyanate, EDA, and N-(2-aminoethyl)-3-aminoethanesulphonic acid, sodium salt) and Baycusan® 1008 (Polyurethane-48, which is a copolymer of adipic acid, 1-6 HDI, NPG, IPDI, IPDA, N-(2-aminoethyl)-3-aminoethanesulpho nic acid, sodium salt) are two products from Bayer Material Science LLC. Polyderm PE-PA ED (Alzo) includes Polyurethane-58.

The problem with the use of WBPUs and WBPU-Us for consumer-based cosmetic products has been the lack of performance and overall consistency in application. For example, common polyurethane products such as Luviset® P.U.R, DynamX, and DynamX $H_2O$ lack elasticity. This leads to an undesirable stiff feeling when applied to hair. Avalure UR 405, Baycusan C1004, Baycusan C1008, and Polyderm PE/PA ED, however, are very flexible (i.e., do not lack elasticity). Yet these products have poor initial curl hold and elicit a gummy feeling. Other problems associated with the use of WBPUs and WBPU-Us include, but are not limited to, flaking upon touching or combing (e.g., dusty micro-flakes shown on hair fibers); undesirable tactile feelings upon touch (e.g., brittle, stiff, or tacky, gummy); poor humidity resistance (e.g., styling resins absorb moisture and weigh down hair resulting in a loss of style); lack of movement (e.g., plastic-like mold shape; hair curls don't move with motion; can't easily comb through; gummy; lack of bounciness); and short-lived hair styles (e.g., hair styles, curls, waves, etc. don't last long—on average styles typically last less than a half day).

What the cosmetic community has been lacking is the existence of selection markers to determine which polyurethanes would result in improved cosmetic performance, and compositions having features within those selection markers which consistency elicit improved performance. Thus identifying selection markers, which when followed affords cosmetic compositions with favorable properties (e.g., long lasting, moisture-resistant hold, and affirmative sensory attributes) solves what has been plaguing the cosmetic industry for years, that is, the need for correlation between the use of certain WBPUs and WBPU-Us and high performance cosmetic products.

SUMMARY

A specific combination of selection markers for WBPU and WBPU-U have now been found that result in cosmetic compositions (e.g., hair fixatives) which have substantially improved performance. This finding overcomes the earlier inconsistencies and flaws associated with commercial polyurethane based products, and provides a solution to the long standing problem of identifying those markers that result in e.g., long lasting, moisture-resistant hold, and favorable sensory attributes. See e.g., the comparative data at Tables 3-6. Such markers include e.g., the mechanical and chemical properties described herein.

Cosmetic compositions comprising WBPUs or WBPU-Us, and which optionally comprise the identified selection markers, are also provided. Compositions operating within the disclosed selection markers were shown to have superior curl shape and sensory attributes under humid conditions when compared to commercially available WBPUs and WBPU-Us. See e.g., Tables 5 and 6.

Further provided are cosmetic compositions comprising WBPU or WBPU-U, together with certain performance-enhancing lipids (e.g., oils). It has been discovered that sensory and tactile attributes associated with a WBPU or WBPU-U hair resin can be modulated with certain performance-enhancing lipids (e.g., oils).

The compositions described herein were shown to provide outstanding results in vivo. See e.g., FIG. 10 where excellent retention of curl shape and definition was achieved even under high humidity conditions. Contrast with e.g., FIG. 11, where the opposite result was achieved using a commercially available composition having markers outside of the scope of those disclosed.

BRIEF DESCRIPTION OF THE DRAWINGS

FIG. 2 is a plot of curled tress length increase in response to a controlled pulling test (mechanical stress test). Tresses treated with inventive polycarbonate polyol-based WBPU-Us possessing the optimal properties (black) have the least curl drop (change in tress length) compared to PCP-based WBPU-Us possessing suboptimal properties (checked pattern), WBPU-Us based on other chemistries (diagonal pattern), and commercial resins (white). Curl drop Δ=(length of curled tress after controlled pull—length of tress at time 0)/(length of tress at time 0)*100 (Method VY-M).

FIG. 13 shows transmission electron microscopic (TEM) images illustrating the optimal particle size and superior particle morphology obtained with the inventive WBPU particles in comparison to commercially available particles, where Panel A and B show the inventive LP PU 299 (having a Young's modulus: 315 MPa, an elongation at break: 47%, and water uptake: 5.95%) at 10,000 × and 30,0000 × magnification respectively; Panel C and D show commercially available DynamX® $H_2O$ at 10,000 × and 30,0000 × magnification respectively; and Panel E and F show commercially available Baycusan® C 1010 at 10,000 × and 30,0000 × magnification respectively.

DETAILED DESCRIPTION

1. Definitions

Figure 1:
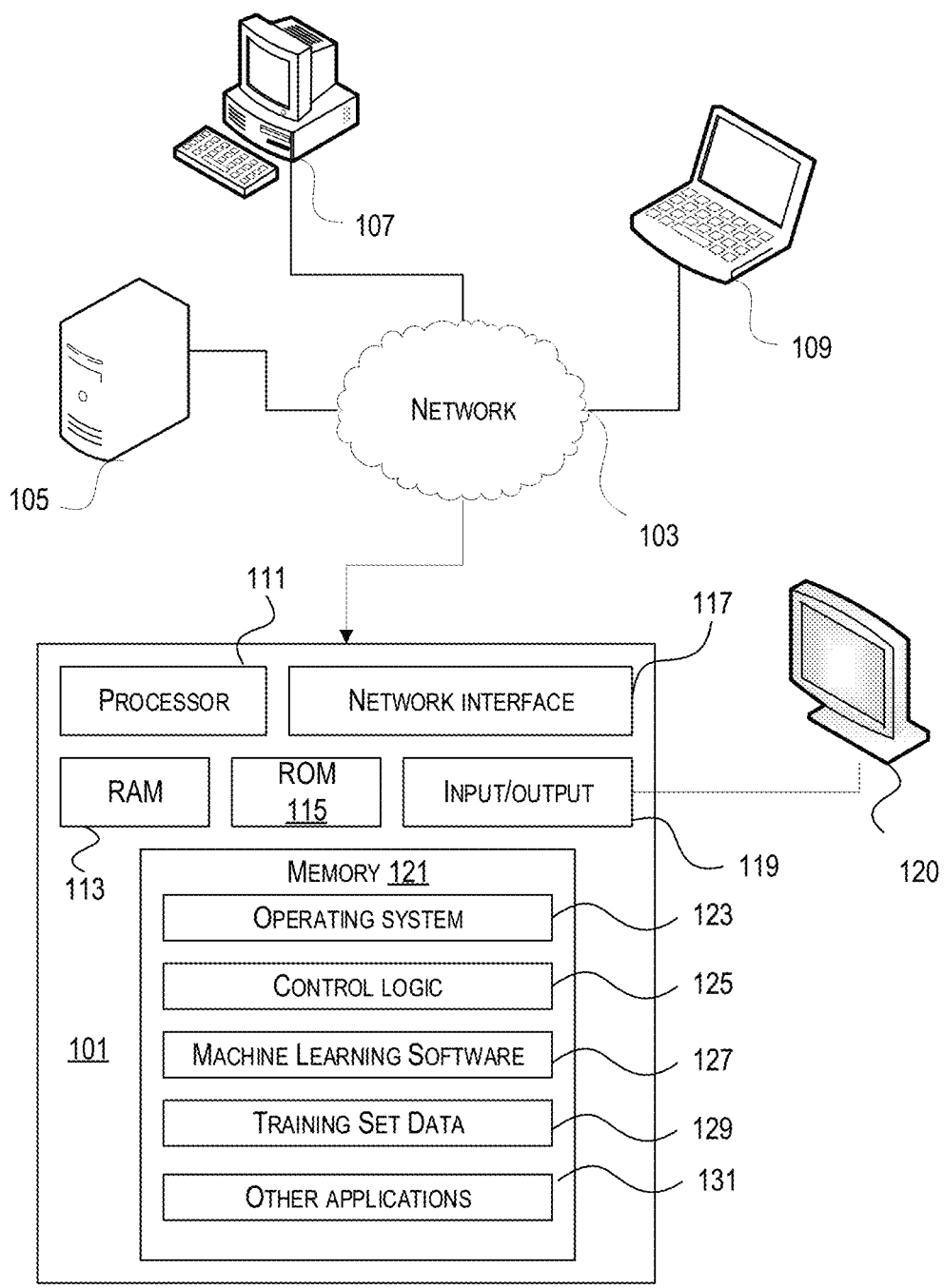
FIG. 1 is a plot depicting the Young's modulus versus elongation at break for inventive polycarbonate polyol-based WBPU-Us (black), suboptimal polycarbonate-polyol based WBPU-Us (dark grey) and commercial resins (light grey). A "suboptimal" polycarbonate-polyol based WBPU-Us was not made using the ratios as described above in the first, second or third embodiments.

The term "alkyl" refers to a monovalent saturated hydrocarbon group. $C_1$-$C_6$ alkyl is an alkyl having from 1 to 6 carbon atoms. An alkyl may be linear or branched. Examples of alkyl groups include methyl; ethyl; propyl, including n-propyl and isopropyl; butyl, including n-butyl, isobutyl, sec-butyl, and t-butyl; pentyl, including, for example, n-pentyl, isopentyl, and neopentyl; and hexyl, including, for example, n-hexyl and 2-methylpentyl.

Unless otherwise specified, "alkylene" by itself or as part of another substituent refers to a saturated straight-chain or branched divalent group having the stated number of carbon atoms and derived from the removal of two hydrogen atoms from the corresponding alkane. Examples of straight chained and branched alkylene groups include —$CH_2$— (methylene), —$CH_2$—$CH_2$—(ethylene), —$CH_2$—$CH_2$—$CH_2$—(propylene), —$C(CH_3)_2$—, —$CH_2$—$CH(CH_3)$—, —$CH_2$—$CH_2$—$CH_2$—$CH_2$—, —$CH_2$—$CH_2$—$CH_2$—$CH_2$—$CH_2$—(pentylene), —$CH_2$—$CH(CH_3)$—$CH_2$—, and —$CH_2$—$C(CH_3)_2$—$CH_2$—.

The term "cycloalkyl" refers to a monocyclic or bicyclic monovalent saturated or non-aromatic unsaturated hydrocarbon ring system. The term "$C_3$-$C_{10}$ cycloalkyl" refers to a cycloalkyl wherein the number of ring carbon atoms is from 3 to 10. Examples of $C_3$-$C_{10}$ cycloalkyl include $C_3$-$C_6$ cycloalkyl. Bicyclic ring systems include fused, bridged, and spirocyclic ring systems. More particular examples of cycloalkyl groups include, cyclopropyl, cyclobutyl, cyclopentyl, cyclohexyl, cycloheptyl, cis- and trans-decalinyl, norbornyl, and spiro[4.5]decanyl.

"Aryl" by itself or as part of another substituent refers to a monovalent aromatic hydrocarbon group having the stated number of carbon atoms (i.e., C5-C14 means from 5 to 14 carbon atoms). Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octophene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthylene, and the like. In a specific embodiment, the aryl group is phenyl or naphthyl.

A "resin" is a polymer that can be used to coat hair and is not limited by physical form (e.g., it can be in solid or liquid form).

A "film" is a resin in solid physical form.

A "polyurethane-urea polymer" refers to a polymer comprising a —O—C(O)—NR2- and a —NR$_2$—C(O)—NR$_2$- linkage. In one aspect, the polyurethane-urea polymer is a thermoplastic polyurethane comprising low polarity segments (called soft segments) alternating with high polarity segments (called hard segments).

"Young's modulus (or the modulus of elasticity, tensile modulus)" is a measure of the stiffness of a solid polymer film. Young's modulus, E, can be calculated by dividing the tensile stress by the extensional strain in the elastic (initial, linear) portion of the stress-strain curve. The Young's modulus of the polyurethane-urea can be determined by a protocol defined to measure mechanical properties, and is developed in reference to ASTM D638, ASTM D412, test guidelines as described below in Example 2.

The "elongation at break (also known as fracture strain, ultimate elongation)" is the ratio between changed length and initial length after breakage of the solid polymer film. The elongation at break of the polyurethane-urea can be determined by a protocol defined to measure mechanical properties, and is developed in reference to ASTM D638, ASTM D412, test guidelines as described below in Example 2.

The "moisture uptake" is the measure of water absorbed by the solid polymer film. The method for determining the moisture uptake of the solid polymer film is provided in Example 3.

"The high humidity mechanical stress test" is a method for evaluating the performance of a hair fixative by applying the fixative to a hair tress hanging the tress under 75% relative humidity at 25° C. for 15 minutes and then mechanically manipulating the tress by extending the tress to its original length, holding for 1 second, and releasing. Tress length recorded at after the controlled pull. The protocol is describes in the Example section as Method VY-HM.

"Sensory Score" is determined by the performance of the hair fixative in Method VY-S as described in Example 4. In particular, the tress with the resin dispersion applied is blow dried for 90 seconds. The tresses are prepared in duplicate and blinded randomly and evaluated for natural feeling and overall sensory attributes on a scale of −2 to 2 by trained sensory analysts under blinded conditions. Sensory analysts are licensed hair stylists and cosmetic scientists with significant long-term experience evaluating sensory attributes of hair. Sensory analysts assign a score of −2 to tresses deemed entirely undesirable, a score of +2 to entirely soft, natural feeling and appearing hair, and intermediate scores between these two extremes.

A "particle" refers to a hydrophobic polymer aggregate formed in response to dispersion in water.

A "performance-enhancing lipid" includes a lipid (e.g., an oil) that, when included with the polyurethane-urea improves the properties of the polyurethane-urea. For example, inclusion of the performance-enhancing lipid may reduce the moisture uptake of the polyurethane-urea, or may improve the sensory properties of the polyurethane-urea with regarding to look and feel of the polyurethane-urea when applied to hair.

The term "lipid" refers to organic compounds which comprise fatty acids or fatty acid derivatives, and are primarily insoluble in water. Lipids include e.g., fats, waxes, sterols, fat-soluble vitamins, monoclycerides, diglycerides, triglycerides, phospholipids, oils, and the like. Lipids may be both liquid or solid at ambient temperature (25° C.) and atmospheric pressure (760 mmHg, i.e. 105 Pa). In one aspect, the lipids described herein are non-volatile oil, where non-volatile refers to, in one aspect, a fatty substance that remains on the skin or the keratin fiber at ambient temperature and atmospheric pressure for at least several hours. In one aspect, non-volatile oils also comprise a vapor pressure of less than 10"3 mmHg (0.13 Pa). In one aspect, oils may be chosen from mineral, animal, plant or synthetic oils. Examples include, but are not limited to fragrance oils, emollients, monoterpenoids, fatty alcohols, fatty acids, fatty esters, fatty ethers, fluorinated small molecules (e.g., perfluoromethylcyclopentane, perfluoroperhydrophenanthrene, perfluoro-1,3-dimethylcyclohexane, perfluoromethyldecalin, and perfluoroperhydrobenzyltetralin), and mixtures thereof.

As used herein, "associated with" in the context of the polyurethane-urea and performance-enhancing lipid complex described herein refers to the interaction of the polyurethane-urea and performance-enhancing lipid. The interaction may involve electrostatic interactions or hydrogen bonding between the polyurethane-urea and the performance-enhancing lipid. Association of the lipid with the polyurethane-urea is driven by its energetically favorable interaction with the organic polymer, as opposed to an energetically unfavorable interaction with water.

A "polyurethane-urea:performance-enhancing lipid complex" comprises a polyurethane-urea and a performance-enhancing lipid (e.g., an oil) in which the performance-enhancing lipid is associated with the polyurethane-urea via non-covalent interactions. In one aspect, the polyurethane-urea:performance-enhancing lipid complex are thermoplastic self-assembled polymer architectures in aqueous medium. Accordingly, the polyurethane-urea does not form a capsule. Furthermore, in at least one embodiment, the polyurethane-urea:performance-enhancing lipid complex is prepared by adding the performance-enhancing lipid to the prepolymer prior to the chain extension step or, alternatively, the performance-enhancing lipid is added following dispersion of the polyurethane-urea into water and, the chain extension step, but prior to removal of the organic solvent. Accordingly, the polyurethane-urea:performance-enhancing lipid complex is not an emulsion. In one aspect, the polyurethane-urea:performance-enhancing lipidcomplex is a unitary complex.

Figure 12:
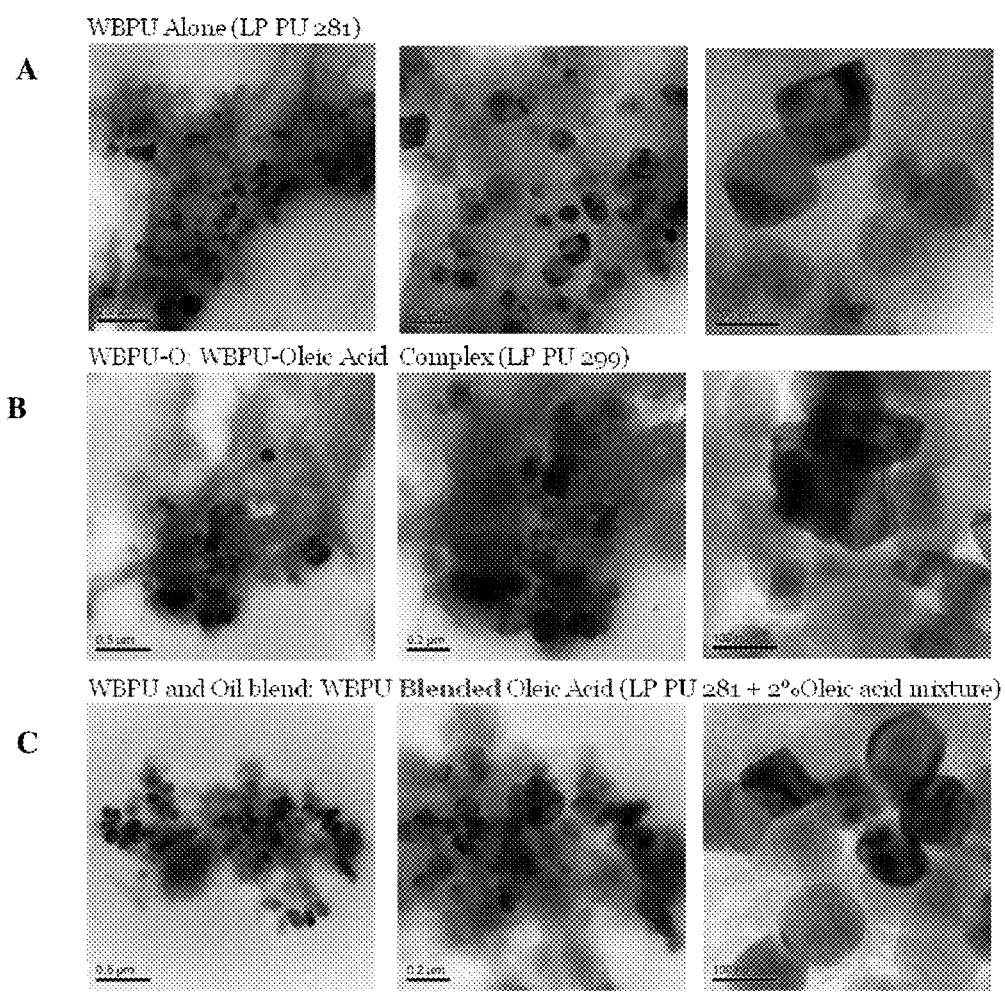
FIG. 12 shows transmission electron microscopy (TEM) images where Panel B shows that the addition of the disclosed lipids (e.g., oil) lead to a morphology that is unique from the morphology of WBPU alone (Panel A) and a simple blend of the WBPU and lipid (Panel C).

As used herein, "unitary complex" refers to unique morphology of the polyurethane-urea:performance-enhancing lipid complex shown by e.g., by FIG. 12, panel B. Panel A of FIG. 12 shows the morphology for WBPU alone. Panel C shows the morphology of WBPU and lipid arising from common blending. Panel B shows the morphology of the polyurethane-urea:performance-enhancing lipid complex, i.e., unitary complex, formed by the methods described herein.

"Fragrance oils" are synthetic or natural oils, which comprise aroma compounds, i.e., those having a smell or odor. Fragrance oils include, but not limited to, cinnamon, cascarilla, rose, jasmine, osmanthus, plumeria, mimosa, tuberose, narcissus, scented gernaium, cassie, ambrette, juniper berry, vanilla, sage, violets, rosemary, myrrh, balsam of Peru, ginger root, cardamom, sandalwood, rosewood, pine, cedar, juniper, orchids, ambergris, civet, hyraceum, honeycomb, musk, ambergris, citronellol, geraniol, nerol, linalool, phenyl ethyl alcohol, farnesol, stearoptene, α-pinene, β-pinene, α-terpinene, limonene, p-cymene, camphene, β-caryophyllene, neral, citronellyl acetate, geranyl acetate, neryl acetate, eugenol, methyl eugenol, rose oxide, α-damascenone, β-damascenone, damascones, benzaldehyde, benzyl alcohol, rhodinyl acetate and phenyl ethyl formate.

"Monoterpenes" are a class of terpenes that consist of two isoprene units and have the molecular formula $C_{10}H_xO_y$, where x is ≤22, and y is between 0 and 2. Monoterpenes may be linear (acyclic) or contain rings. Representative monoterpens include menthol, isoborneol, geraniol, terpineol, limonene, myrcene, linalool, pinene, and iridoids.

A "Fatty Alcohol" is hydrocarbons that include a primary alcohol. A hydrocarbon includes only hydrogen and carbon and can be saturated or unsaturated. For example, the fatty alcohol may include from 3 to 40 carbons, from 4 to 36 carbon, from 5 to 30 carbons, from 8 to 25 carbon, from 12 to 20 carbons. Representative fatty alcohols include tent-Butyl alcohol, tent-Amyl alcohol, 3-Methyl-3-pentanol, Ethchlorvynol, 1-Octanol, Pelargonic alcohol, 1-Decanol (decyl alcohol, capric alcohol), Undecyl alcohol (1-undecanol, undecanol, Hendecanol), Lauryl alcohol (Dodecanol, 1-dodecanol), Tridecyl alcohol (1-tridecanol, tridecanol, isotridecanol), Myristyl alcohol (1-tetradecanol), Pentadecyl alcohol (1-pentadecanol, pentadecanol), Cetyl alcohol (1-hexadecanol), Palmitoleyl alcohol (cis-9-hexadecen-1-ol), Heptadecyl alcohol (1-n-heptadecanol, heptadecanol), Stearyl alcohol (1- octadecanol), Oleyl alcohol, Nonadecyl alcohol (1-nonadecanol), Arachidyl alcohol (1-eicosanol), Heneicosyl alcohol (1-heneicosanol), Behenyl alcohol (1-docosanol), Erucyl alcohol (cis-13-docosen-1-ol), Lignoceryl alcohol (1-tetracosanol), Ceryl alcohol (1-hexacosanol), 1-Heptacosanol, Montanyl alcohol, cluytyl alcohol, or 1-octacosanol, 1-Nonacosanol, Myricyl alcohol, melissyl alcohol, or 1-triacontanol, 1-Dotriacontanol (Lacceryl alcohol), Geddyl alcohol (1-tetratriacontanol), or Cetearyl alcohol.

A "Fatty acid" is a carboxylic acid with a long aliphatic chain, which is either saturated or unsaturated. For example, the fatty acid may include from 3 to 40 carbons, from 4 to 36 carbon, from 5 to 30 carbons, from 8 to 25 carbon, from 12 to 20 carbons. Representative fatty acids include, but are not limited to, Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, Docosahexaenoic acid, Caprylic acid, Capric acid, Lauric acid, Myristic acid, Palmitic acid, Stearic acid, Arachidic acid, Behenic acid, Lignoceric acid, or Cerotic acid.

A "Fatty Ester" is a type of ester that results from the combination of a fatty acid with an alcohol. For example, the fatty ester may include from 3 to 40 carbons, from 4 to 36 carbon, from 5 to 30 carbons, from 8 to 25 carbon, from 12 to 20 carbons. Representative examples include hexyl laurate and glyceryl laurate.

A "Fatty Ether" is a carboxylic acid with a long aliphatic chain, which is either saturated or unsaturated. For example, the fatty ether may include from 3 to 40 carbons, from 4 to 36 carbon, from 5 to 30 carbons, from 8 to 25 carbon, from 12 to 20 carbons. Representative fatty acids include, but are not limited to, dicaprylyl ether.

An "emollient" includes any material that has a softening or smoothing sensory effect, and includes but not limited to fatty alcohols, fatty acids, fatty esters and fatty ethers.

2. Selection Markers

Provided herein are specific combinations of WBPU and WBPU-U properties that have been found to result in cosmetic compositions (e.g., hair fixatives) having substantially improved performance. Those properties include e.g., a combination of certain mechanical properties, a combination of certain chemical properties, or a combination of both mechanical and chemical properties.

Young's Modulus, Elongation at Break, and Moisture Uptake

The combination of mechanical properties described herein include the Young's modulus (e.g., above 150 MPa), the elongation at break (e.g., from about 15% to about 300%), and hydrophobicity (moisture uptake, e.g., less than 10%).

In one aspect, the Young's modulus of the polyurethane-urea should be above about 150 MPa. For example, the Young's modulus of the polyurethane-urea in the disclosed compositions may be above about 160 MPa, above about 170 MPa, above about 180 MPa, above about 190 MPa, above about 200 MPa, above about 210 MPa, above about 220 MPa, above about 230 MPa, above about 240 MPa, above about 250 MPa, above about 260 MPa, above about 270 MPa, above about 280 MPa, above about 290 MPa, above about 300 MPa, above about 310 MPa, above about 320 MPa, above about 330 MPa, above about 340 MPa, above about 350 MPa, above about 360 MPa, above about 370 MPa, above about 380 MPa, above about 390 MPa, above about 400 MPa, above about 410 MPa, above about 420 MPa, above about 430 MPa, above about 440 MPa, above about 450 MPa, above about 460 MPa, above about 470 MPa, above about 480 MPa, above about 490 MPa, above about 500 MPa, above about 510 MPa, above about 520 MPa, above about 530 MPa, above about 540 MPa, or above 550 MPa. In other aspects, the Young's modulus of the polyurethane-urea should be between about 150 MPa and about 500 MPa. For example, the Young's modulus of the polyurethane-urea in the disclosed compositions may be between about 150 MPa and about 400 MPa, between about 170 MPa and about 390 MPa, between about 180 MPa and about 320 MPa, between about 190 MPa and about 300 MPa, between about 200 MPa and about 290 MPa, or between about 210 MPa and about 280 MPa.

In one aspect, the elongation at break of the polyurethane-urea should be from about 15% to about 300%. For example, the elongation at break of the polyurethane-urea in the disclosed composition may be from about 20% to about 300%, from about 40% to about 280%, from about 100% to about 280%, from about 100% to about 250%, from about 150% to about 250%, from about 200% to about 250%, from about 210% to about 250%, about 30 to about 150%, from about 15% to about 150%, from about 150% to about 300%, from about 50 to about 250%; from about 75 to about 225%, or from about 100 to about 200%. The elongation break may be optionally combined with one or more of the Young's modulus values described in the paragraph above or any one of the Young's modulus values described in the remainder of the disclosure.

In one aspect, the moisture uptake of the polyurethane-urea should be less than about 10%. For example, the moisture uptake of the polyurethane-urea in the disclosed compositions may be less than about 9.5%, less than about 9%, less than about 8.5%, less than about 8%, less than about 7.5%, less than about 7%, less than about 6.5%, less than about 6%, less than about 5.5%, less than about 5%, less than about 4.5%, less than about 4%, less than about 3.5%, less than about 3%, less than about 2.5%, less than about 2%, less than about 1.5%, less than about 1%, less than about 0.5%, or is about 0%. In one aspect, the moisture uptake of the polyurethane-urea in the disclosed compositions should be from about 0% to about 10%. For example, the moisture uptake may be from about 0% to about 8%, from about 2% to about 8%, or from about 3% to about 7%. The moisture uptake may be optionally combined with one or more of the Young's modulus values, one or more of the elongation break values, or both as described in the paragraphs above or in the remainder of the disclosure.

As shown in the Exemplification section below, polyurethane-ureas having the Young's modulus, elongation at break, and moisture uptake described above have improved performance (e.g., long lasting, moisture-resistant hold, and favorable sensory attributes).

Additional Markers

In addition to the Young's modulus, elongation at break, and moisture uptake, other markers may be used to identify the capability of WBPU and WBPU-U to provide long lasting, moisture-resistant hold hair product with favorable sensory attributes. Such markers include e.g., change in tress length, sensory score, and particle size.

Thus, in certain aspects, the polyurethane-urea may be selected such that the composition, after being applied to a curled hair tress and dried thereon, provides less than about 80% change in tress length as measured by the high humidity mechanical stress test. For example, the polyurethane-urea may be selected such that the composition, after being applied to a curled hair tress and dried thereon, provides less than about 75%, about 70%, about 65%, about 60%, about 55%, about 50%, about 45%, about 40%, about 35%, about 30%, about 25%, about 20%, about 15%, about 10%, about 5%, or about 0% change in tress length as measured by the high humidity mechanical stress test. The change in tress length as described herein may also be combined with any one of the Young's modulus values, elongation at break values, and moisture uptake values described above and herein.

In other aspects, the polyurethane-urea may be selected such that the composition, after being applied to a hair tress and dried thereon, provides a sensory score of at least about 0. For example, the polyurethane-urea in the disclosed compositions may be selected such that the composition, after being applied to a hair tress and dried thereon, provides a sensory score of at least about 0.1, about 0.2, about 0.3, about 0.4, about 0.5, about 0.6, about 0.7, about 0.8, about 0.9, about 1.0, about 1.1, about 1.2, about 1.3, about 1.4, or about 1.5. The sensory score feature as described herein may also be combined with any one of the change in tress length values, the Young's modulus values, the elongation at break values, and the moisture uptake values described above and herein.

In other aspects, the polyurethane-urea may be selected such that the polyurethane-urea dispersed in water forms a polyurethane-urea particle with a particle size of less than about 200 nm. For example, the polyurethane-urea particle formed may have a particle size of less than about 190 nm, less than about 180 nm, less than about 170 nm, less than about 160 nm, less than about 150 nm, less than about 140 nm, less than about 130 nm, less than about 120 nm, less than about 110 nm, less than about 100 nm, less than about 90 nm, less than about 80 nm, less than about 70 nm, less than about 60 nm, less than about 50 nm, or less than about 40 nm. The particle size feature as described herein may be combined with the any one of the sensory score values, the change in tress length values, the Young's modulus values, the elongation at break values, and the moisture uptake values described above and herein.

As shown in the Exemplification section below, polyurethane-ureas having the Young's modulus, elongation at break, and moisture uptake described above, and optionally one of more of the alternative markers (e.g., sensory score, particle size in water, change in tress length, etc.) provide hair styling products that are resistant to mechanical disturbances (e.g., touching of the hair with objects) and moisture changes in the environment, and provide a pleasing sensory impression. See e.g., Tables 5 and 6.

3. Compositions

Provided herein are compositions comprising polyurethane-ureas, wherein the Young's modulus of the polyurethane-urea is above 150 MPa; the elongation at break of polyurethane-urea is from about 15% to about 300%; and the moisture uptake of the polyurethane-urea is less than 10%.

In some aspects, the composition, after being applied to a curled hair tress and dried thereon, provides less than 80% change in tress length as measured by the high humidity mechanical stress test.

In other aspects, the composition, after being applied to a hair tress and dried thereon, provides a sensory score of at least 0.

In other aspects, the polyurethane-urea, when dispersed in water, forms a polyurethane-urea particle. In a further aspect, the particle size of the polyurethane-urea particle is less than 200 nm or as described in the selection marker section above. In yet a further aspect, the particle size of the polyurethane-urea particle is less than 200 nm (or as defined in the selection marker section above) and the moisture uptake of the polyurethane-urea is less than 10%, or as described in the selection marker section above.

In some aspects, the polyurethane-urea in the compositions described herein comprises a soft segment and a hard segment. In some instances, the soft segment is formed from a polyol comprising a polyester, polyether, or polycarbonate or combination of thereof; and the hard segment is formed from a polyisocyanate, an ionic chain extender, and at least one of a non-ionic polyol chain extender and a diamine chain extender. In one aspect, the soft segment is formed from a polyol comprising a polyester and the hard segment is formed from a polyisocyanate, an ionic chain extender, and at least one of a non-ionic polyol chain extender and a diamine chain extender.

In one aspect, the polyol of the soft segment is formed from a dihydric alcohol and an aliphatic, cycloaliphatic, or aromatic polycarboxylic acid or polycarboxylic acid anhydride; wherein the polycarboxylic acid is selected from succinic, glutaric, adipic, pimelic, suberic, azelaic, sebacic, nonanedicarboxylic, decanedicarboxylic, terephthalic, isophthalic, o-phthalic, tetrahydrophthalic, hexahydrophthalic and trimellitic acid, and the polycarboxylic acid anhydride is selected from o-phthalic, trimellitic, succinic acid anhydride and a mixture thereof; the dihydric alcohol selected from ethanediol, diethylene, triethylene, tetraethylene glycol, 1,2-propanediol, dipropylene, tripropylene, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, 1,8-octanediol, 1,10-decanediol, 1,12-dodecanediol, and mixtures thereof.

In one aspect, the polyol of the soft segment is a homopolymer or copolymer of lactones obtained by an addition reaction of lactones or lactone mixtures and dihydric alcohols reacted with diaryl, dialkyl or cycloalkyl carbonates; wherein the lactone is selected from butyrolactone, ε-caprolactone and methyl-ε-caprolactone; and the dihydric alcohol is selected from ethanediol, diethylene, triethylene, tetraethylene glycol, 1,2-propanediol, dipropylene, tripropylene, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, 1,8-octanediol, 1,10-decanediol, 1,12-dodecanediol or mixtures thereof. In another aspect, the polyol of the soft segment is polycaprolactonediol.

In one aspect, the polyol of the soft segment is formed from a polyether polyol. In another aspect, the polyol of the soft segment is formed from the reaction of water, dihydric alcohols selected from ethanediol, diethylene, triethylene, tetraethylene glycol, 1,2-propanediol, dipropylene, tripropylene, tetrapropylene glycol, 1,3-propanediol, 1,4-butanediol, 1,3-butanediol, 2,3-butanediol, 1,5-pentanediol, 1,6-hexanediol, 2,2-dimethyl-1,3-propanediol, 1,4-dihydroxycyclohexane, 1,4-dimethylolcyclohexane, 1,8-octanediol, 1,10-decanediol, 1,12-dodecanediol and mixtures thereof with alkylene oxides selected from ethylene oxide; propylene oxide; butylene oxide; styrene oxide; tetrahydrofuran or epichlorohydrin and with mixtures of these alkylene oxides.

In one aspect, the polyol of the soft segment is formed is formed from a polycarbonate polyol. In another aspect, the polyol comprises a polycarbonate obtained from the reaction of one or more diols with one or more diarylcarbonates, dialkylcarbonates or cycloalkylcarbonates. The diol may be selected from (1,3)-propanediol, (1,4)-butanediol, (1,5)-pentanediol, (1,6)-hexanediol, diethylene glycol, triethylene glycol or tetraethylene glycol and the diarylcarbonate, dialkylcarbonate or cycloalkylcarbonate is selected from diphenyl carbonate, dimethyl carbonate, diethylcarbonate, ethylene carbonate, propylene carbonate, carbonic acid, or phosgene.

In one aspect, the polyol of the soft segment is selected from a polycarbonate polyol made from reacting (1,6)-hexanediol with a diarylcarbonate, dialkylcarbonate or cycloalkylcarbonate; a polycarbonate polyol made from reacting blend of (1,6)-hexanediol and (1,5)-pentanediol with diarylcarbonate, dialkylcarbonate or cycloalkylcarbonate; and a polycarbonate polyol made from reacting blend of caprolactone and (1,6)-hexanediol with diarylcarbonate, dialkylcarbonate or cycloalkylcarbonate.

In one aspect, the polyisocyanate of the hard segment is represented by the general formula $R^6(NCO)_2$; wherein $R^6$ represents a divalent hydrocarbon group having from 4 to 20 carbon atoms and containing 0, 1, or 2 cycloalkyl or aromatic groups. In another aspect, the polyisocyanate are the hard segment is selected from tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane, 1,3- and 1,4-bis(isocyanatomethyl)-cyclohexane, bis-(4-isocyanato-3-methyl-cyclohexyl)-methane, 1,5-diisocyanato naphthalene, 4,4'-methylenebis(cyclohexyl isocyanate) (H12MDI) and norbornene diisocyanate. In yet another aspect, the polyisocyanate of the hard segment is isophorone diisocyanate or 4,4'-Methylenebis(cyclohexyl isocyanate) (H12MDI). The polyisocyanate as described in this paragraph and herein may be combined with the polyester, polyether, or polycarbonate or combination thereof as described in the preceding paragraphs and herein.

In one aspect, the ionic chain extender of the hard segment comprises a functional group selected from a carboxylic acid and an amine In some aspects, the ionic chain extender of the hard segment is selected from the group consisting of dimethylolpropionic acid, dimethylolbutyric acid, and 3-dimethylamino-1,2-propanediol. In one aspect, the ionic chain extender is lysine. The ionic chain extender as described in this paragraph and herein may be combined with the polyisocyanates, polyesters, polyethers, or polycarbonates or combinations thereof as described in the preceding paragraphs and herein.

In one aspect, the non-ionic polyol chain extender of the hard segment is a $C_1$-$C_8$alkyldiol. In another aspect, the non-ionic polyol chain extender of the hard segment is selected from the group consisting of 1,4-butanediol, 1,5-pentandiol, and 1,6-hexanediol. The non-ionic polyol chain extender described in this paragraph and herein may be combined with the ionic chain extender, polyisocyanates, polyesters, polyethers, or polycarbonates or combinations thereof as described in the preceding paragraphs and herein.

In one aspect, the diamine chain extender of the hard segment is represented by formula $NH_2R^1NH_2$, wherein the $R^1$ is a $C_1$-$C_8$alkyl optionally substituted with —(O)OH. The diamine chain extender described in this paragraph and herein may be combined with the non-ionic polyol chain extender, ionic chain extender, polyisocyanates, polyesters, polyethers, or polycarbonates or combinations thereof as described in the preceding paragraphs and herein.

In one aspect, the polyurethane-urea is represented by structural formula (I):

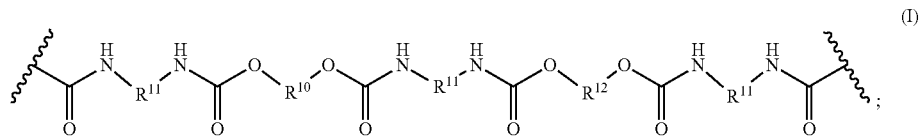

(I)

or a cosmetically acceptable salt thereof; wherein each $R^{10}$ is $—(C(R^{10a})_2)_p[O(C=O)OC((R^{10a})_2)_qO(C=O)OC((R^{10a})_2)_r]_x—$;

each $R^{10a}$ is independently selected from H and $C_{1-6}$alkyl;

p is an integer from 1 to 10;

q is an integer from 1 to 10;

r is an integer from 1 to 10;

x is an integer from 2 to 25;

each $R^{11}$ is independently selected from a divalent hydrocarbon group having from 4 to 20 carbon atoms and containing 0, 1, or 2 cycloalkyl or aromatic groups;

each $R^{12}$ is a divalent group independently selected from a $C_1$-$C_8$alkylene optionally substituted with —$COOR^{12a}$ or —$(CH_2)_mNR^{12a}$;

each $R^{12a}$ is independently selected from hydrogen and $C_1$-$C_4$alkyl; and m is an integer from 0 to 6. In one aspect for the polyurethane-ureas represented by structural Formula (I) the Young's modulus of the polyurethane-urea is above 150 MPa and the elongation at break is from about 15% to about 300%. Alternative values for the Young's modulus and elongation break are included and are described above.

In another aspect, the polyurethane-urea is represented by structural formula (II):

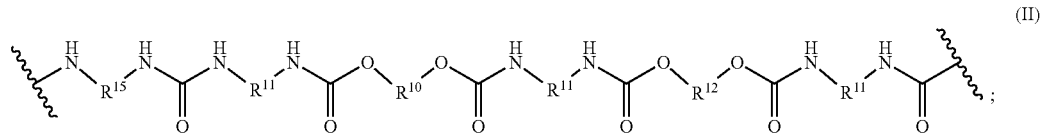

or a cosmetically acceptable salt thereof; wherein
each $R^{15}$ is independently a $C_1$-$C_8$alkylene substituted with —$(CH_2)_n COOR^{15a}$;
each $R^{15a}$ is independently selected from hydrogen or $C_1$-$C_4$alkyl;
n is an integer from 0 to 6; and
m is an integer from 0 to 6. In one aspect for the polyurethane-ureas represented by structural Formula (II) the Young's modulus of the polyurethane-urea is above 150 MPa and the elongation at break is from about 15% to about 300%. Alternative values for the Young's modulus and elongation break are included and are described above.

In another aspect, the polyurethane-urea is represented by structural Formula (IIIa) or (IIIb):

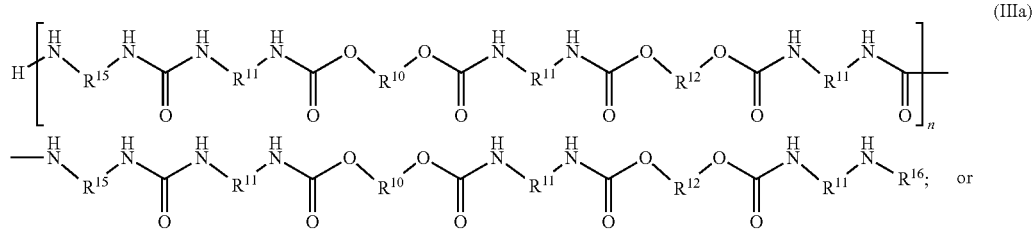

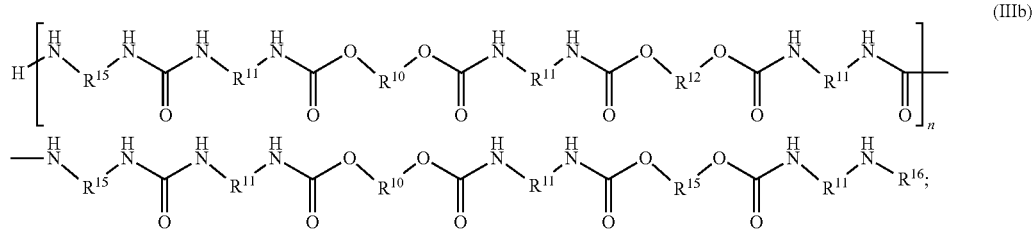

or a cosmetically acceptable salt thereof; wherein
$R^{16}$ is H or —C(O)—NH—$R^{15}$—$NH_2$; and
n is an integer from 3-50, wherein the values of the remaining variables are as described above for Formula (I) and Formula (II). In one aspect for the polyurethane-ureas represented by structural Formula (IIIa) and (IIIb) the Young's modulus of the polyurethane-urea is above 150 MPa and the elongation at break is from about 15% to about 300%. Alternative values for the Young's modulus and elongation break are included and are described above.

In one aspect, the polyurethane-urea is of structural formula (I), (II), (IIIa) or (IIIb), wherein p is an integer from 4 to 8; q is an integer from 4 to 8; r is an integer from 4 to 8; and x is an integer from 5 to 25.

In one aspect, the polyurethane-urea is of structural formula (I), (II), (IIIa) or (IIIb), wherein each $R^{11}$ is independently selected from a divalent hydrocarbon group selected from $C_1$-$C_{15}$alkylene,

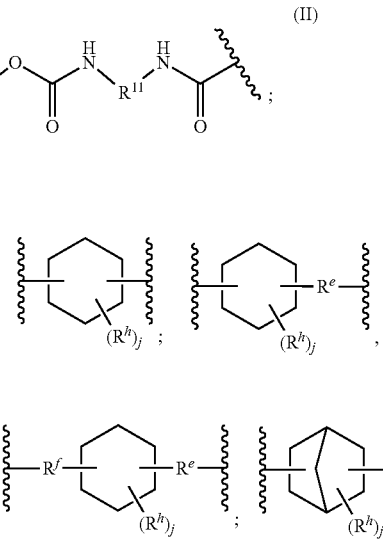

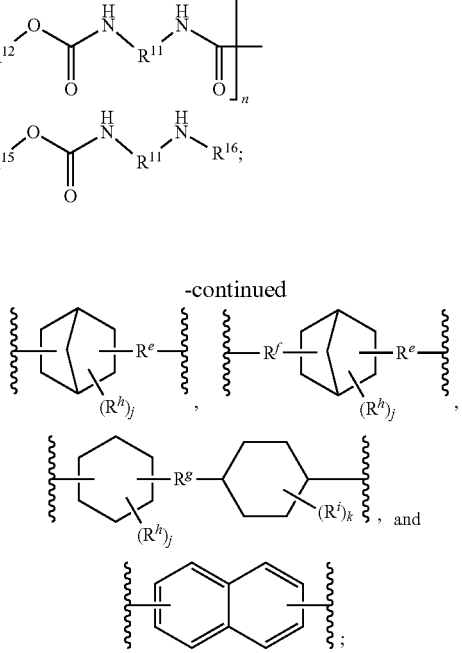

wherein each $R^c$, $R^f$, and $R^g$ is $C_1$-$C_4$alkylene; each $R^h$ and $R^i$ is independently selected from H or $C_1$-$C_4$alkyl; and j and k are each integers from 0 to 10, wherein the values for the remaining variables are as described above.

In one aspect, the polyurethane-urea is of structural formula (I), (II), (IIIa) or (IIIb), wherein $R^{11}$ is selected from one of the following structural formula:

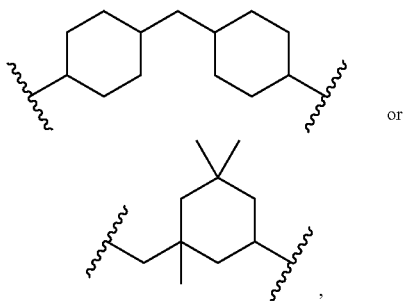

wherein the values for the remaining variables are as described above.

In one aspect, the polyurethane-urea is of structural formula (I), (II), (IIIa) or (IIIb), wherein each $R^{12}$ is a divalent group independently selected from a methylene, ethylene, propylene, butylene, pentylene, and hexylene, each optionally substituted with —COOH or —$CH_2N(CH_3)_2$; wherein the values for the remaining variables are as described above.

In one aspect, the polyurethane-urea is of structural formula (II), (IIIa) or (IIIb), wherein each $R^{15}$ is independently ethylene, propylene, butylene, pentylene, and hexylene, each optionally substituted with —COOH; wherein the values for the remaining variables are as described above.

In another aspect, the polyurethane-ureas described herein may be formed from a first embodiment of monomer units of W, X, Y and $Z^1$ and $Z^2$, wherein
  W is a polycarbonate polyol;
  X is a polyisocyanate;
  Y is an anionic chain extender; and
  $Z^1$ is a non-ionic polyol chain extender;
  $Z^2$ is a diamine chain extender, wherein the diamine is substituted with —COOH;
wherein
  the molecular weight of W is about 1,000 g/mol;
  the ratio of X:W is from about 1:0.23 to about 1:0.47;
  the ratio of X:Y is from about 1:0.2 to about 1:0.3;
  the ratio of X:$Z^1$ is from about 1:0 to about 1:0.13; and
  the ratio of X:$Z^2$ is from about 1:0.03 to about 1:0.46.

In one aspect of the first embodiment of monomer units, the anionic chain extender is, for example, dimethylolpropionic acid or dimethylolbutyric acid. Alternatively, the first embodiment of monomer units is formed from monomer units of W, X, Y and $Z^1$ and $Z^2$, wherein
  W is a polycarbonate polyol;
  X is a polyisocyanate;
  Y is an cationic chain extender; and
  $Z^1$ is a non-ionic polyol chain extender;
  $Z^2$ is a diamine chain extender, wherein the diamine is substituted with —COOH;
wherein
  the molecular weight of W is about 1,000 g/mol;
  the ratio of X:W is from about 1:0.23 to about 1:0.47;
  the ratio of X:Y is from about 1:0.2 to about 1:0.33;
  the ratio of X:$Z^1$ is from about 1:0 to about 1:0.3; and
  the ratio of X:$Z^2$ is from about 1:0 to about 1:0.46. In one aspect of this first embodiment of monomer units, the cationic chain extender is 3-dimethylamino-1,2-propanediol.

In another aspect, the polyurethane-ureas described herein may be formed from a second embodiment of monomer units of W, X, Y and $Z^1$ and $Z^2$, wherein
  W is a polycarbonate polyol;
  X is a polyisocyanate;
  Y is an anionic chain extender; and
  $Z^1$ is a non-ionic diol chain extender; and
  $Z^2$ is a diamine chain extender, wherein the diamine is substituted with —COOH;
wherein
  the molecular weight of W is about 2,000 g/mol;
  the ratio of X:W is from about 1:0.05 to about 1:0.27;
  the ratio of X:Y is from about 1:0.16 to about 1:0.33;
  the ratio of X:$Z^1$ is from about 1:0.02 to about 1:0.5; and
  the ratio of X:$Z^2$ is from about 1:0.03 to about 1:0.47.

In one aspect of the second embodiment of monomer units, the anionic chain extender is, for example, dimethylolpropionic acid or dimethylolbutyric acid. Alternatively, the second embodiment of the invention is a polyurethane-urea formed from monomer units of W, X, Y and $Z^1$ and $Z^2$, wherein
  W is a polycarbonate polyol;
  X is a polyisocyanate;
  Y is an cationic chain extender; and
  $Z^1$ is a non-ionic polyol chain extender;
  $Z^2$ is a diamine chain extender, wherein the diamine is substituted with —COOH;
wherein
  the molecular weight of W is about 2,000 g/mol;
  the ratio of X:W is from about 1:0.05 to about 1:0.27;
  the ratio of X:Y is from about 1:0.16 to about 1:0.33;
  the ratio of X:$Z^1$ is from about 1:0.02 to about 1:0.5; and
  the ratio of X:$Z^2$ is from about 1:0 to about 1:0.47. In an aspect of this second embodiment, the cationic chain extender is 3-dimethylamino-1,2-propanediol.

In another aspect, the polyurethane-ureas described herein may be formed from a third embodiment of monomer units of W, X, Y and $Z^1$ and $Z^2$, wherein
  W is a polycarbonate polyol;
  X is a polyisocyanate;
  Y is an anionic chain extender; and
  $Z^1$ is a non-ionic diol chain extender; and
  $Z^2$ is a diamine chain extender, wherein the diamine is substituted with —COOH;
wherein
  the molecular weight of W is about 3,000 g/mol;
  the ratio of X:W is from about 1:0.02 to about 1:0.2;
  the ratio of X:Y is from about 1:0.16 to about 1:0.34;
  the ratio of X:$Z^1$ is from about 1:0.02 to about 1:0.52; and
  the ratio of X:$Z^2$ is from about 1:0.03 to about 1:0.49.

Alternatively, the third embodiment of monomer units may be formed from monomer units of W, X, Y and $Z^1$ and $Z^2$, wherein
  W is a polycarbonate polyol;
  X is a polyisocyanate;
  Y is an cationic chain extender; and
  $Z^1$ is a non-ionic polyol chain extender;
  $Z^2$ is a diamine chain extender, wherein the diamine is substituted with —COOH;
wherein
  the molecular weight of W is about 3,000 g/mol;
  the ratio of X:W is from about 1:0.02 to about 1:0.2;
  the ratio of X:Y is from about 1:0.16 to about 1:0.34;

the ratio of X:Z$^1$ is from about 1:0.02 to about 1:0.52; and
the ratio of X:Z$^2$ is from about 1:0 to about 1:0.49. In a particular aspect of this third embodiment, the cationic chain extender is 3-dimethylamino-1,2-propanediol.

In a fourth embodiment of monomer units, the polyurethane-urea is formed from the monomers units of W, X, Y and Z$^1$ and Z$^2$ as described for the first, second and third embodiments of monomer units, wherein the polycarbonate polyol is obtained from the reaction of one or more diols with one or more diarylcarbonates, dialkylcarbonates, cycloalkylcarbonates, carbonic acid or acid halides. In another aspect, the diol is selected from (1,3)-propanediol, (1,4)-butanediol, (1,5)-pentanediol, (1,6)-hexanediol, diethylene glycol, triethylene glycol or tetraethylene glycol and the diarylcarbonate, dialkylcarbonate, cycloalkylcarbonate, carbonic acid or acid halides is selected from diphenyl carbonate, dimethyl carbonate, diethylcarbonate, ethylene carbonate, propylene carbonate, carbonic acid, or phosgene.

In a fifth embodiment of monomer units, the polyurethane-urea is formed from the monomers units of W, X, Y and Z$^1$ and Z$^2$ as described for the first, second and third embodiments of monomer units, wherein the polycarbonate polyol is selected from a polycarbonate polyol made from reacting (1,6)-hexanediol with a diarylcarbonate, dialkylcarbonate, cycloalkylcarbonate, carbonic acid or acid halides; a polycarbonate polyol made from reacting blend of (1,6)-hexanediol and (1,5)-pentanediol with a diarylcarbonate, dialkylcarbonate, cycloalkylcarbonate, carbonic acid or acid halides; and a polycarbonate polyol made from reacting butylethylpropanediol with a diarylcarbonate, dialkylcarbonate, cycloalkylcarbonate, carbonic acid or acid halides.

In a sixth embodiment of monomer units, the polyurethane-urea is formed from the monomers units of W, X, Y and Z$^1$ and Z$^2$ as described for the first, second and third embodiments of monomer units, wherein the polyisocyanate is represented by the general formula R$^6$(NCO)$_2$; wherein R$^6$ represents a divalent hydrocarbon group having from 4 to 20 carbon atoms and containing 1 or 2 cycloalkyl or aromatic groups, and the remainder of the monomer units are as described for the first, second, third, fourth or fifth embodiments. In an aspect of the sixth embodiment, each R$^6$ is independently selected from a divalent hydrocarbon group selected from C$_1$-C$_{15}$alkylene,

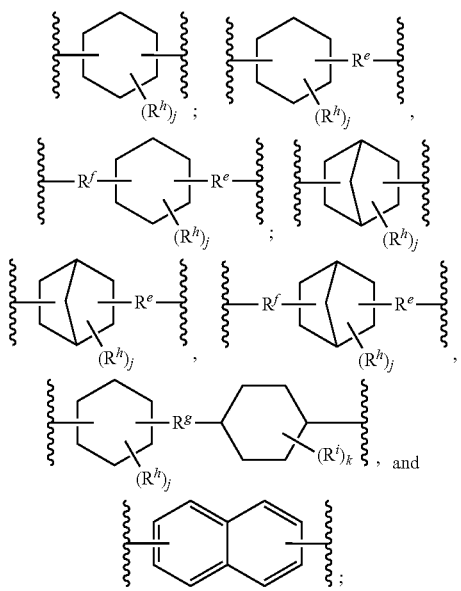

wherein each R$^e$, R$^f$, and R$^g$ is C$_1$-C$_4$alkylene; each R$^h$ and R$^i$ is independently selected from H or C$_1$-C$_4$alkyl; and j and k are each integers from 0 to 10, and the remainder of the monomer units are as described for the first, second, third, fourth or fifth of monomer unit embodiments. In one aspect, each R$^6$ is independently selected from one of the following structural formula:

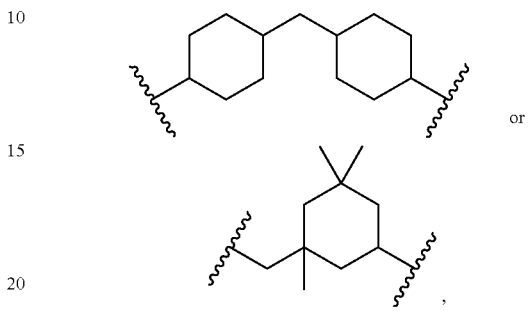

and the remainder of the monomer units are as described for the first, second, third, fourth or fifth of monomer unit embodiments.

In a seventh embodiment of monomer units, the polyurethane-urea is formed from the monomers units of W, X, Y and Z$^1$ and Z$^2$ as described for the first, second and third of monomer unit embodiments, wherein the polyisocyanate is selected from tetramethylene diisocyanate, 1,6-hexamethylene diisocyanate, dodecamethylene diisocyanate, cyclohexane-1,3- and -1,4-diisocyanate, 1-isocyanato-3-isocyanatomethyl-3,5,5-trimethylcyclohexane (isophorone diisocyanate or IPDI), bis-(4-isocyanatocyclohexyl)-methane (H$_{12}$MDI), 1,3- and 1,4-bis(isocyanatomethyl)-cyclohexane, bis-(4-isocyanato-3-methyl-cyclohexyl)-methane, and 1,5-diisocyanato naphthalene, and norbornene diisocyanate, and the remainder of the monomer units are as described for the first, second, third, fourth, or fifth of monomer unit embodiments.

In an eighth embodiment of monomer units, the polyurethane-urea is formed from the monomers units of W, X, Y and Z$^1$ and Z$^2$ as described for the first, second and third of monomer unit embodiments, wherein the polyisocyanate is selected from isophorone diisocyanate and H$_{12}$MDI, and the remainder of the monomer units are as described for the first, second, third, fourth or fifth of monomer unit embodiments.

In a ninth embodiment of monomer units, the polyurethane-urea is formed from the monomers units of W, X, Y and Z$^1$ and Z$^2$ as described for the first, second and third of monomer unit embodiments, wherein the wherein the ionic chain extender is a compound with a molecular weight of 500 g/mol or less, wherein the remainder of the monomer units are as described for the first, second, third, fourth, fifth, sixth, seventh, and eighth of monomer unit embodiments.

In a tenth embodiment of monomer units, the polyurethane-urea is formed from the monomers units of W, X, Y and Z$^1$ and Z$^2$ as described for the first, second and third of monomer unit embodiments, wherein the ionic chain extender comprises a functional group that is selected from a carboxylic acid or amine, wherein the remainder of the monomer units are as described for the first, second, third, fourth, fifth, sixth, seventh, eighth, and ninth of monomer unit embodiments.

In an eleventh embodiment of monomer units, the polyurethane-urea is formed from the monomers units of W, X, Y and Z$^1$ and Z$^2$ as described for the first, second and third of monomer unit embodiments, wherein the ionic chain extender is selected from the group consisting of dimethylolpropionic acid, dimethylolbutyric acid, and 3-dimethylamino-1,2-propanediol, wherein the remainder of the monomer units are as described for the first, second, third, fourth, fifth, sixth, seventh, eighth, ninth, and tenth of monomer unit embodiments.

In a twelfth embodiment of monomer units, the polyurethane-urea is formed from the monomers units of W, X, Y and $Z^1$ and $Z^2$ as described for the first, second and third of monomer unit embodiments, wherein $Z^1$ has molecular weight of 500 g/mol or less and $Z^2$ has a molecular weight of 500 g/mol or less, wherein the remainder of the monomer units are as described for the first, second, third, fourth, fifth, sixth, seventh, eighth, ninth and tenth of monomer unit embodiments. Alternatively, the polyurethane-urea is formed from the monomer units of W, X, Y and $Z^2$ as described for the first, second and third of monomer unit embodiments, wherein $Z^1$ is absent and $Z^2$ has a molecular weight of 500 g/mol or less, wherein the remainder of the monomer units are as described for the first, second, third, fourth, fifth, sixth, seventh, eighth, ninth, tenth, and eleventh of monomer unit embodiments.

In a thirteenth embodiment of monomer units, the polyurethane-urea is formed from the monomers units of W, X, Y and $Z^1$ and $Z^2$ as described for the first, second and third of monomer unit embodiments, $Z^1$ is a $C_{1-10}$alkyldiol or polyoligosilesquioxane diol and $Z^2$ is $C_{1-10}$alkyldiamine substituted with —COOH, wherein the remainder of the monomer units are as described for the first, second, third, fourth, fifth, sixth, seventh, eighth, ninth, tenth, eleventh, and twelfth of monomer unit embodiments. In one embodiment, $Z^1$ is 1,4-butanediol or 1,6-hexanediol and $Z^2$ is lysine. Alternatively, the polyurethane-urea is formed from the monomers units of W, X, Y and $Z^2$ as described for the first, second and third embodiments, wherein $Z^1$ is absent and $Z^2$ is $C_{1-10}$alkyldiamine substituted with —COOH, wherein the remainder of the monomer units are as described for the first, second, third, fourth, fifth, sixth, seventh, eighth, ninth, tenth, eleventh, and twelfth of monomer unit embodiments. In one embodiment, $Z^1$ is absent and $Z^2$ is lysine.

In certain aspects, the polyurethane-ureas described herein can be dispersed in an aqueous solution suitable for use in personal care products. In some embodiments, the dispersion further includes a volatile hydrophobicity enhancer. In one aspect, the volatile hydrophobicity enhancer is encapsulated within the dispersed polyurethane-urea. Alternatively, the volatile hydrophobicity enhancer is not covalently bonded to the polyurethane. In one aspect, the volatile hydrophobicity enhancer is 2,2,3,3,4,4,5,5-octafluoropentyl methacrylate (OFPMA), a hydrocarbon such as squalene, or a hydrocarbon derivative such as ionone or 18-methyl eicosanoic acid. In one aspect, the volatile hydrophobicity enhancer is 2,2,3,3,4,4,5,5-octafluoropentyl methacrylate (OFPMA). In certain aspects, the volatile hydrophobicity enhancer increases the hydrophobicity (i.e., reduces the water uptake) of the polyurethane-urea. In one aspect, the hydrophobicity enhancer reduces the water uptake of the WBPU-U to less than 8%, for example, less than 7.5%, less than 7.0%, less than 6.5%, less than 6.0%, less than 5.5%, less than 5.0%, less than 4.5%, less than 4.0%, less than 3.5%, less than 3.0%, less than 2.5%, less than 2.0%, less than 1.5%, or less than 1.0%. The hydrophobicity of the polyurethane-urea can be determined by methods known to one of skill in the art. For example, the method as described in Example 3, below, can be used In certain aspects, the polyurethane-ureas described herein may be neutralized with a neutralizer. The neutralizer may be selected from an acid or base. In some aspects, the neutralizer is selected from $Na_2CO_3$, triethylamine, tributylamine, tripentylamine, trihexylamine, trioctylamine, or lactic acid.

In one aspect, the neutralizer:ionic chain extender ratio is from about 0.8 to about 1.2 In some aspects, the neutralizer:ionic chain extender ratio is from about 0.8 to about 1.0; alternatively it is 1.0:1.2; alternatively it is 1:1.

In certain aspects, the compositions described herein further comprise a performance enhancing lipid. Thus, the present disclosure provides a composition comprising any one of the polyurethane-ureas or properties (e.g., Young's modulus, elongation at break, moisture uptake, etc.), or both, described herein together with a performance-enhancing lipid. In one aspect, the moisture uptake is less than 8% when a performance enhancing lipid is present.

In some aspects, the performance-enhancing lipid is associated with polyurethane-urea to form a polyurethane-urea:performance-enhancing lipid complex. In certain aspects, the polyurethane-urea:performance-enhancing lipid complex is dispersed in water.

In some aspects, the polyurethane-urea:performance-enhancing lipid complex is a unitary complex.

Performance-enhancing lipid can be selected from fragrance oils, emollients, monoterpenoids, fatty alcohols, fatty acids, fatty esters, fatty ethers, fluorinated small molecules (e.g., perfluoromethylcyclopentane, perfluoroperhydrophenanthrene, perfluoro-1,3-dimethylcyclohexane, perfluoromethyldecalin, and perfluoroperhydrobenzyltetralin), and mixtures thereof. In some aspects, the performance-enhancing lipid is selected from cinnamon, cascarilla, rose, jasmine, osmanthus, plumeria, mimosa, tuberose, narcissus, scented gernaium, cassie, ambrette, juniper berry, vanilla, sage, violets, rosemary, myrrh, balsam of Peru, ginger root, cardamom, sandalwood, rosewood, pine, cedar, juniper, orchids, ambergris, civet, hyraceum, honeycomb, musk, ambergris, citronellol, geraniol, nerol, linalool, phenyl ethyl alcohol, farnesol, stearoptene, α-pinene, β-pinene, α-terpinene, limonene, p-cymene, camphene, β-caryophyllene, neral, citronellyl acetate, geranyl acetate, neryl acetate, eugenol, methyl eugenol, rose oxide, α-damascenone, β-damascenone, damascones, benzaldehyde, benzyl alcohol, rhodinyl acetate and phenyl ethyl formate, tert-Butyl alcohol, tent-Amyl alcohol, 3-Methyl-3-pentanol, Ethchlorvynol, 1-Octanol, Pelargonic alcohol, 1-Decanol (decyl alcohol, capric alcohol), Undecyl alcohol (1-undecanol, undecanol, Hendecanol), Lauryl alcohol (Dodecanol, 1-dodecanol), Tridecyl alcohol (1-tridecanol, tridecanol, isotridecanol), Myristyl alcohol (1-tetradecanol), Pentadecyl alcohol (1-pentadecanol, pentadecanol) , Cetyl alcohol (1-hexadecanol), Palmitoleyl alcohol (cis-9-hexadecen-1-ol), Heptadecyl alcohol (1-n-heptadecanol, heptadecanol), Stearyl alcohol (1-octadecanol), Oleyl alcohol, Nonadecyl alcohol (1-nonadecanol), Arachidyl alcohol (1-eicosanol), Heneicosyl alcohol (1-heneicosanol), Behenyl alcohol (1-docosanol), Erucyl alcohol (cis-13-docosen-1-ol), Lignoceryl alcohol (1-tetracosanol), Ceryl alcohol (1-hexacosanol), 1-Heptacosanol, Montanyl alcohol, cluytyl alcohol, or 1-octacosanol, 1-Nonacosanol, Myricyl alcohol, melissyl alcohol, or 1-triacontanol, 1-Dotriacontanol (Lacceryl alcohol), Geddyl alcohol (1-tetratriacontanol), Cetearyl alcohol, Myristoleic acid, Palmitoleic acid, Sapienic acid, Oleic acid, Elaidic acid, Vaccenic acid, Linoleic acid, Linoelaidic acid, α-Linolenic acid, Arachidonic acid, Eicosapentaenoic acid, Erucic acid, Docosahexaenoic acid, Caprylic acid, Capric acid, Lauric acid, Myristic acid, Palmitic acid, Stearic acid, Arachidic acid, Behenic acid, Lignoceric acid, Cerotic acid, β-Ionone, α-Ionone, 7,8-dihydro-α-Ionone, dihydro-β-Ionone, squalene, hemisqualane, methyl eugenol, damascone, citronellol, psuedoionone, caryophyllene, geraniol, limonene, linalool, linoleic acid, menthol, carvone, isoborneol, eucalyptol, camphor, α-pinene, resveratrol, linolenic acid, palmitic acid, myristyl alcohol, cetyl alcohol, oleyl alcohol, octadecanol, hexyl laurate, glyceryl laurate, dicaprylyl ether, octafluoropentyl methacrylate, stearic acid, oleic acid, ethylhexyl palmitate, octyl stearate, isostearyl alcohol, isoamyl laurate or mixtures thereof.

In one aspect, the performance-enhancing lipid is selected from an omega-3, an omega-6, or an omega-9 fatty acid. In other aspects, the performance-enhancing lipid is a polyphenol, a flavonoid. In yet another aspect, the performance-enhancing lipid is a phytochemical.

The compositions described herein may further comprise an antioxidant. Antioxidants that may be suitable with the compositions described herein include, but are not limited to, açai oil, alpha lipoic acid, green and white tea, retinol, vitamin C, Vitamin E, coenzyme Q10 (Co Q-10), isoflavones, polyphenols, curcumin, turmeric, pomegranate, rosemary, glutathione, selenium, and zinc.

4. Methods of Use

The compositions described herein may be used for any cosmetic application. Such applications include, but are not limited to, skin-care creams, eye and facial makeup (e.g., mascara, eye liner, eyebrow makeup, and the like), deodorants, lotions, powders, perfumes, baby products, body butters; and hair products (e.g., permanent chemicals, hair colors, hair sprays, and gels).

In one aspect, the compositions described herein are used as a hair product, e.g., in a conventional manner for providing hairstyle/hold benefits. In an exemplary aspect, an effective amount of a composition described herein may be sprayed or applied onto dry or damp hair before and/or after the hair is styled. As used herein "effective amount" means an amount sufficient to provide the hair hold and style performance desired according to the length and texture of the hair.

In one aspect, the present disclosure provides a method of fixing hair comprising the step of applying a polyurethane-urea disclosed herein. In one aspect, the present disclosure provides a method of retaining the curl of hair comprising the step of applying polyurethane-urea disclosed herein.

In one aspect, the present disclosure also includes a method to determine the curl retention of a hair tress. In one aspect, the method of measuring the curl retention of a hair tress includes the steps of a) measuring the length of the hair tress; b) applying a composition comprising a waterborne polyurethane-urea disclosed herein to the hair tress; c) blow drying the hair tress for 90 seconds without brushing; d) curling the hair tress with a ¾ inch curling rod at 370° F. for 10 seconds; e) mechanically manipulating the hair tress by pulling, combing and brushing; f) measuring the length of the curled hair tress.

In one aspect, the method of measuring the curl retention of a hair tress, includes the steps of a) measuring the length of the hair tress; b) applying the composition comprising a waterborne polyurethane-urea disclosed herein to the hair tress; c) blow drying the hair tress for 90 seconds without brushing; d) curling the hair tress with a ¾ inch curling rod at 370° F. for 10 seconds; e) subjecting the hair tress to humidity; f) measuring the length of the curled hair tress. In one aspect, the curled hair tress is subjected to 60%, 70%, 75%, 80% or 90% relative humidity for 5, 10, 15, 20, 25, 30, 35, 40, 45, 50, 55, 60, 75, 90, 105,120, 180 or 210 minutes at a temperature of 25° C.

In one aspect, the method of measuring the curl retention of a hair tress, includes the steps of a) measuring the length of the hair tress; b) applying the composition comprising a waterborne polyurethane-urea disclosed herein to the hair tress; c) blow drying the hair tress for 90 seconds without brushing; d) curling the hair tress with a ¾ inch curling rod at 370° F. for 10 seconds; e) subjecting the hair tress to humidity; f) brushing the hair tress; g) measuring the length of the curled hair tress. In a particular aspect, the curled hair tress is subjected to 60%, 70%, 75%, 80% or 90% relative humidity for 2, 4, 8, 16, 32, or 48 hours at a temperature of 25° C. and brushed 1, 3, 5, 8, 10, 13, 15, or 20 times.

In one aspect, the method of evaluating the curl retention of a hair tress, includes the steps of a) applying the composition comprising a polyurethane-urea disclosed herein to the hair tress; b) blow drying the hair tress for 90 seconds without brushing; c) blinding the prepared hair tress; d) evaluating the sensory properties of the tress in a blinded fashion. In one aspect, the prepared tress is graded on a scale of −2 to 2 for natural feeling and overall sensory attributes.

In one aspect, the polyurethane-urea is selected such that the composition, after being applied to a curled hair tress and dried thereon, performs better than Baycusan C1004 (Polyurethane-35) in the high humidity mechanical stress test.

In another aspect, the polyurethane-urea is selected such that the composition, after being applied to a curled hair tress and dried thereon, performs better than Baycusan C1004 (Polyurethane-35) in the sensory test.

4. General Processes of Preparing Polyurethane-Ureas

The present disclosure also includes a method of preparing the polyurethane-ureas disclosed herein. In one aspect, the process includes preparing a prepolymer of formula having the values describe above by: 1) reacting at least one polyol, at least one polyisocyanates, and at least one ionic diol chain extender; and optionally, at least one non-ionic diol chain extender; 2) chain-extending the prepolymer with at least one diamine chain extender, wherein the diamine is substituted with —COOH; 3) dispersing the polyurethane in water; and 5) removing the organic solvent, resulting in an aqueous polyurethane dispersion.

Also contemplated herein are polyurethane dispersions. Methods for forming a polyurethane dispersion comprise e.g., (a) reacting (1) at least one polyisocyanate, and (2) at least one polyol, (3) at least one compound having at least one hydrophilic, ionic or potentially ionic group, and (4) non-ionic diol in order to form an isocyanate terminated prepolymer; wherein an effective amount of at least one performance-enhancing lipid is introduced into the reaction at any time during prepolymer formation; and (b) subsequently (1) dispersing said polymer in water and (2) chain extending said prepolymer by reaction with at least one diamine chain extender to form a polyurethane-urea polymer, wherein the Young's modulus of the polyurethane-urea: performance-enhancing lipid complex is above 150 MPa; the elongation at break is from about 15% to above 300%; and the moisture uptake of the polyurethane-urea is less than 8%.

Alternatively, the process comprises (a) reacting (1) at least one polyisocyanate, and (2) at least one polyol, and (3) at least one compound having at least one hydrophilic, ionic or potentially ionic group, and (4) at least one non-ionic diol in order to form an isocyanate terminated prepolymer; and (b) subsequently (1) dispersing said polymer in water. and (2) chain extending said prepolymer by reaction with at least a diamine chain extender to form a polyurethane-urea polymer, and (3) adding an effective amount of at least one performance-enhancing lipid to the polymer, wherein the Young's modulus of the polyurethane-urea:performance-enhancing lipid complex is above 150 MPa; the elongation at break is from about 15% to above 300%; and the moisture uptake of the polyurethane-urea is less than 10%.

In one aspect, the polyurethane-urea product made from the above processes are dispersed in water to form a polyurethane-urea particle with a particle size of less than 200 nm; and wherein the moisture uptake of the polyurethane-urea is less than 8%.

Other methods for preparing the polyurethane-ureas disclosed herein will be apparent to those skilled in the art.

EXEMPLIFICATION

Example 1

Synthesis of Polycarbonate Poly-Based WBPU-Us

Synthesis of PU 126. Polycarbonate 1k polyol (PCP) was first dried at 110° C. under reduced pressure until it was bubble free. A 500 mL three neck glass reactor equipped with condenser, magnetic stirrer, argon inlet, oil bath, and heat/stir plate was purged with argon and charged with PCP1k (0.032 mol). The reactor was heated to 80° C. for 0.5 h. Isophorone diisocyanate (IPDI) (0.1 mol) was added dropwise to the reactor and the mixture was then allowed to stir for 1 h. The temperature was then brought down to 60° C., and zinc neodecanoate (0.1 g) in 5 mL of acetone was added into the reactor dropwise. Dimethylol butyric acid (DMBA) (0.024 mol) was pre-mixed with 25 mL acetone and added to the reactor. The reaction was stirred at 60° C. for 16 h under argon. The next day, the reaction temperature was brought down to 30° C., and neutralizing base $Na_2CO_3$ (0.012 mol) was added to the reactor for neutralization of the DMBA. The reaction continued for 1 h while stirring at 500 rpm. Stirring speed was increased to 900 rpm and 150 mL of deionized water was added dropwise (4-5 mL/min) to the reactor using an addition funnel. L-Lysine (0.044 mol) dissolved in 10 mL water was added in the reaction mixture and allowed to react for 2 h while stirring at 500 rpm. A nearly clear dispersion resulted. The acetone was then removed from the dispersion. The present solid content was determined by exhaustive drying of a 1 g sample.

The synthesis described above for PU 126 can be modified to prepare the WBPU-Us listed in Table 1, below. In particular, PU 150, PU 154, PU 182, PU 187, PU 189, and PU 192 to PU196 were prepared with the same protocol as PU 126 with further encapsulation of an additive (30-50 wt %) after WBPU-U synthesis.

PU 161, PU 154, and PU 160 were prepared with the same protocol as PU 126 with substitution of the $Na_2CO_3$ neutralizer for triethylamine (TEA).

PU 188 and PU 198 were prepared with the same protocol as PU 126 with the substitution of DMBA for 3-dimethyl-amino-1,2-propanediol (DMAPD), and subsequent neutralization with lactic acid.

PU 144, 160, 162, PU 176, 187, 188, 189, 191, 192, and 195-199 were prepared with the same protocol as PU 126 with the addition of another diol alongside the addition of the ionic chain extender.

PU 200 was prepared with the same protocol as PU126 except with substitution of IPDI for $H_{12}MDI$.

TABLE 1

| PU Name | NCO | Polyol (molar ratio to NCO) | Other diol Segment (molar ratio to NCO) | Ionic Chain Extender (molar ratio to NCO) | Non Ionic Chain Extender (molar ratio to NCO) | Neutralizer | Additive |
|---|---|---|---|---|---|---|---|
| Examples of inventive polycarbonate polyol-based WBPU-Us | | | | | | | |
| 126 | IPDI | PCP1k_0.32 | NA | DMBA_0.24 | L-Lysine_0.44 | $Na_2CO_3$ | NA |
| 127 | IPDI | PCP1k_0.45 | NA | DMBA_0.28 | L-Lysine_0.27 | $Na_2CO_3$ | NA |
| 128 | IPDI | PCP1k_0.32 | NA | DMBA_0.24 | L-Lysine_0.44 | $Na_2CO_3$ | NA |
| 129 | IPDI | PCP1k_0.45 | NA | DMBA_0.28 | L-Lysine_0.27 | $Na_2CO_3$ | NA |
| 141 | IPDI | PCP1k_0.43 | NA | DMBA_0.28 | L-Lysine_0.29 | $Na_2CO_3$ | NA |
| 144 | IPDI | PCP1k_0.3 | BD_0.04 | DMBA_0.24 | L-Lysine_0.36 | $Na_2CO_3$ | NA |
| 150 | IPDI | PCP1k_0.45 | NA | DMBA_0.28 | L-Lysine_0.27 | $Na_2CO_3$ | OFPMA |
| 151 | IPDI | PCP1k_0.45 | NA | DMBA_0.28 | L-Lysine_0.27 | $Na_2CO_3$ | NA |
| 152 | IPDI | PCP1k_0.45 | NA | DMBA_0.28 | L-Lysine_0.27 | $Na_2CO_3$ | NA |
| 153 | IPDI | PCP2k_0.24 | NA | DMBA_0.31 | L-Lysine_0.45 | $Na_2CO_3$ | NA |
| 154 | IPDI | PCP1k_0.45 | NA | DMBA_0.28 | L-Lysine_0.27 | TEA | OFPMA |
| 160 | IPDI | PCP1k_0.3 | BD_0.04 | DMBA_0.24 | L-Lysine_0.36 | TEA | NA |
| 161 | IPDI | PCP1k_0.32 | NA | DMBA_0.24 | L-Lysine_0.44 | TEA | NA |
| 162 | IPDI | PCP1k_0.3 | BD_0.13 | DMBA_0.23 | L-Lysine_0.19 | $Na_2CO_3$ | NA |
| 167 | IPDI | PCP1k_0.45 | NA | DMBA_0.28 | L-Lysine_0.27 | $Na_2CO_3$ | NA |
| 174 | IPDI | PCP1k_0.45 | NA | DMBA_0.28 | L-Lysine_0.27 | $Na_2CO_3$ | NA |
| 176 | IPDI | PCP2k_0.07 | HD_0.26 | DMBA_0.18 | L-Lysine_0.25 | $Na_2CO_3$ | NA |
| 182 | IPDI | PCP1k_0.45 | NA | DMBA_0.28 | L-Lysine_0.27 | $Na_2CO_3$ | OFPMA |
| 187 | IPDI | PCP1k_0.3 | BD_0.04 | DMBA_0.24 | L-Lysine_0.36 | $Na_2CO_3$ | OFPMA |
| 188 | IPDI | PCP1k_0.27 | BD_0.18 | DMAPD_0.27 | NA | Lactic acid | NA |
| 189 | IPDI | PCP1k_0.3 | BD_0.13 | DMBA_0.23 | L-Lysine_0.19 | $Na_2CO_3$ | OFPMA |
| 191 | IPDI | PCP1k_0.25 | HD_0.11 | DMBA_0.22 | L-Lysine_0.21 | $Na_2CO_3$ | NA |
| 192 | IPDI | PCP1k_0.25 | HD_0.11 | DMBA_0.22 | L-Lysine_0.21 | $Na_2CO_3$ | OFPMA |
| 193 | IPDI | PCP1k_0.45 | NA | DMBA_0.28 | L-Lysine_0.27 | $Na_2CO_3$ | OFPMA |
| 195 | IPDI | PCP1k_0.3 | BD_0.13 | DMBA_0.23 | L-Lysine_0.19 | $Na_2CO_3$ | Squalene |
| 196 | IPDI | PCP1k_0.3 | BD_0.13 | DMBA_0.23 | L-Lysine_0.19 | $Na_2CO_3$ | Ionone |
| 197 | IPDI | PCP1k_0.43 | BD_0.1 | DMBA_0.27 | L-Lysine_0.06 | $Na_2CO_3$ | NA |
| 198 | IPDI | PCP1k_0.42 | BD_0.1 | DMAPD_0.33 | NA | Lactic acid | NA |
| 199 | IPDI | PCP1k_0.3 | BD_0.13 | DMBA_0.23 | L-Lysine_0.19 | $Na_2CO_3$ | NA |

TABLE 1-continued

| PU Name | NCO | Polyol (molar ratio to NCO) | Other diol Segment (molar ratio to NCO) | Ionic Chain Extender (molar ratio to NCO) | Non Ionic Chain Extender (molar ratio to NCO) | Neutralizer | Additive |
|---|---|---|---|---|---|---|---|
| 200 | $H_{12}$MDI | PCP1k_0.34 | BD_0.04 | DMBA_0.25 | L-Lysine_0.11 | $Na_2CO_3$ | NA |
| Examples of sub-optimal polycarbonate polyol-based WBPU-Us ||||||||
| 184 | IPDI | PCP1k_0.2 | HD_0.3 | DMBA_0.2 | L-Lysine_0.55 | $Na_2CO_3$ | NA |
| 185 | IPDI | PCP1k_0.2 | HD_0.22 | DMBA_0.19 | L-Lysine_0.2 | $Na_2CO_3$ | NA |
| 194 | IPDI | PCP1k_0.2 | HD_0.22 | DMBA_0.19 | L-Lysine_0.2 | $Na_2CO_3$ | OFPMA |
| Non-polycarbonate polyol-based WBPU-Us ||||||||
| 103 | IPDI | PEtP1k_0.34 | NA | DMBA_0.3 | L-Lysine_0.37 | $Na_2CO_3$ | NA |
| 104 | IPDI | PEtP1k_0.49 | NA | DMBA_0.35 | L-Lysine_0.16 | $Na_2CO_3$ | NA |
| 105 | IPDI | PEtP1k_0.34 | NA | DMBA_0.3 | L-Lysine_0.37 | $Na_2CO_3$ | NA |
| 106 | IPDI | PEtP1k_0.34 | NA | DMBA_0.3 | L-Lysine_0.37 | $Na_2CO_3$ | NA |
| 122 | IPDI | PEtP1k_0.15 | BD_0.14 | DMBA_0.22 | L-Lysine_0.27 | $Na_2CO_3$ | NA |
| 130 | IPDI | PCP/PEP2k_0.25 | NA | DMBA_0.31 | L-Lysine_0.44 | $Na_2CO_3$ | NA |
| 134 | IPDI | PEtP1k_0.34 | BD_0.06 | DMBA_0.3 | L-Lysine_0.23 | $Na_2CO_3$ | NA |
| 135 | IPDI | PEtP1k_0.33 | BD_0.11 | DMBA_0.29 | L-Lysine_0.27 | $Na_2CO_3$ | NA |
| 136 | IPDI | PEtP1k_0.34 | BD_0.03 | DMBA_0.3 | L-Lysine_0.29 | $Na_2CO_3$ | NA |
| 138 | IPDI | PEtP1k_0.34 | BD_0.08 | DMBA_0.29 | L-Lysine_0.17 | $Na_2CO_3$ | NA |
| 140 | IPDI | PCP/PEP2k_0.25 | NA | DMBA_0.31 | L-Lysine_0.44 | $Na_2CO_3$ | NA |
| 142 | IPDI | PCP/PEP2k_0.45 | NA | DMBA_0.28 | L-Lysine_0.27 | $Na_2CO_3$ | NA |
| 171 | IPDI | PCP/PEP2k_0.16 | BD_0.14 | DMBA_0.25 | L-Lysine_0.37 | TEA | OFPMA |
| 172 | IPDI | PEtP1k_0.32 | NA | DMAPD_0.35 | NA | Lactic acid | NA |
| 173 | IPDI | PEtP1k_0.15 | HD_0.52 | DMBA_0.22 | NA | $Na_2CO_3$ | NA |

Nomenclature: IPDI: isophorone diisocyanate; $H_{12}$MDI: bis-(4-isocyanatocyclohexyl)-methane; PCP1k: polycarbonate polyol having 1k g/mol molecular weight; PEtP1k: polyether polyol having 1k g/mol molecular weight; PCP/PEP2k: polycarbonate and polyester copolyol having 2k g/mol molecular weight; BD: butanediol; HD: hexanediol; DMBA: dimethylol butyric acid; DMAPD: 3-dimethylamino-1,2-propanediol; TEA: triethylamine; OFPMA: 2,2,3,3,4,4,5,5-octafluoropentyl methacrylate.

Example 2

Mechanical Performance

The Young's modulus is a measure of the ability of a material to withstand changes in length when under uniaxial tension or compression. A higher Young's modulus typically indicates that the material is more rigid. The elongation at break, also known as fracture strain, is the ratio between changed length and initial length after breakage of the test specimen. A higher elongation at break expresses the capability of a material to resist fracture. For a composition applied to hair to hold the shape of the hair, the Young's modulus and elongation at break of the composition should be such that the composition provides rigidity to the hair but is not brittle.

A comparison of Young's modulus and the elongation at break for the some of the polyurethane-ureas disclosed herein was made to several commercially available polyurethane products. The Young's modulus and the elongation at break can be determined by a protocol defined to measure mechanical properties is developed in compliance with ASTM D638, ASTM D412, test guidelines. In particular, the following protocol can be used to determine the Young's modulus and elongation at break (or ultimate elongation) of dry film of polyurethanes (WBPUs) and polyurethane-ureas (WBPU-Us). Testing requires ~10-20 min per sample to complete.

Materials:
>25 g polyurethane-urea aqueous dispersion
1 clean rectangle mold (2 mm×20 mm×45 mm) grooved on Teflon sheet per sample
1 clean razor blade
Scotch tape
Universal Testing Machine mounted with extension grip geometry Sample Preparation:
1. Prepare 25 g of 10 wt % WBPU or WBPU-U solution from their respective stock solution.
2. Apply 2.5 mL prepared solution in each mold (2 mm'20 mm×45 mm) and allow drying for 2 days to give WBPU-U film.
3. After it dries out, use a spatula to remove film from the mold.
4. Use the razor blade to cut corners and get film with around 15 mm width and around 150-300 micron thickness. Make sure that the film is free of air bubbles.
5. Label the test film.
6. Cut four pieces of scotch tape (20 mm) per sample and adhere them to both sides of the specimen strip and make a dog-bone shaped sample to improve hold of sample in grip. Store the prepared test films in desiccators for 1-2 hour to fully dry them. Take one sample out of desiccators at a time for testing.

Sample Testing
1. Balance the load registering on the universal testing machine so that it reads 0 Newtons.
2. Use calipers to set a distance of 20 mm between the top and bottom extension grip geometries.
3. Mount a sample in the extension grips and secure tightly, ensuring that the scotch tape is not visible, and that the sample is as close to vertical as possible in both vertical planes
4. Stretch the sample slightly, by separating the geometries until a force of 2-5 N is registered.
5. Begin a tensile testing run on the universal testing machine at a speed of 100 mm/minute, stopping the test upon sample fracture.

6. Elongation at break is calculated at the elongation at which the material fractures.

7. Young's modulus is calculated as the modulus during the initial, elastic portion of deformation by calculating the slope of a linear fit to that region with an R value>0.99.

FIG. 1 is a plot depicting the Young's modulus versus elongation at break, and shows that the commercially resins tend to have:

a) low modulus and high elongation (Avaluare UR 450, C1004, Polyderm PE/PA ED, Polyderm PE/PA), which leads to inferior curl hold (e.g., hold is temporary, transient, or short-lived) or b) high modulus and low elongation (DynamX, DynamX/H2O, Luviset PUR), which leads to a brittle material with low performance (e.g., resin is brittle or fractures) after manipulation.

Example 3

Hydrophobicity/Water Uptake of Polyurethane-Urea

The moisture uptake properties, under highly humid environment, of WBPU or WBPU-U dry films have been linked to their long lasting hold performance. As such, it is important to be able to reproducibly and accurately evaluate such moisture uptake properties to enable predictive in vitro evaluation of WBPU-U dry films. The following protocol can be used to determine moisture uptake ability of WBPU-U dry films under high humid environment. Test requires ~2-3 days per sample set to complete Materials >15 g WBPU-U solution 1 clean cell culture petri dish (60 mm dia×15 mm H) per sample Humidity chamber with flexibility to control temperature and relative humidity (RH)

Sample Testing

1. Prepare 15 g of 10 wt % WBPU-U solution from their respective stock solution.

2. Label cell culture petri dishes for each sample and measure their empty weight ($W_{pd}$).

3. Apply 4 mL prepared solution in each petri dish (3 samples per WBPU or WBPU-U solution) and allow to dry for 20 hours at 25° C. and 50% RH in humidity chamber.

4. After drying out, measure and record sample weight ($W_i$).

5. Place the samples to humidity chamber at 25° C. and 90% RH and allow equilibrating to high humidity for 20 hours.

6. Measure and record final sample weight ($W_f$).

Sample Analysis

Calculate % moisture uptake using the following equation:

$$\% \text{ moisture uptake} = \left[\frac{((Wf - Wpd) - (Wi - Wpd))}{(Wi - Wpd)}\right] \times 100\%$$

Example 4

Hair Fixative Performance

Figure 5:
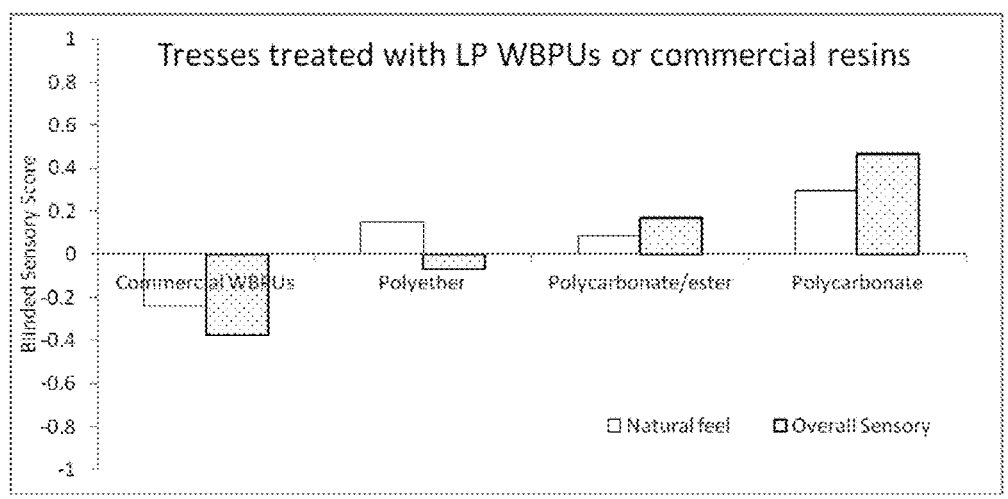
FIG. 5 is a plot showing scores for natural feeling and overall sensory performance from blinded sensory grading by trained sensory evaluators. Overall sensory scores take into account softness, piecyness, stiffness, and gumminess of prepared samples. Tresses treated with the inventive polycarbonate-based WBPU-Us outperform tresses treated with WBPU-Us containing non-polycarbonate soft segments, and also outperform commercial WBPU-Us DyanmX $H_2O$ and Luviset PUR (Method VY-S).
Figure 6:
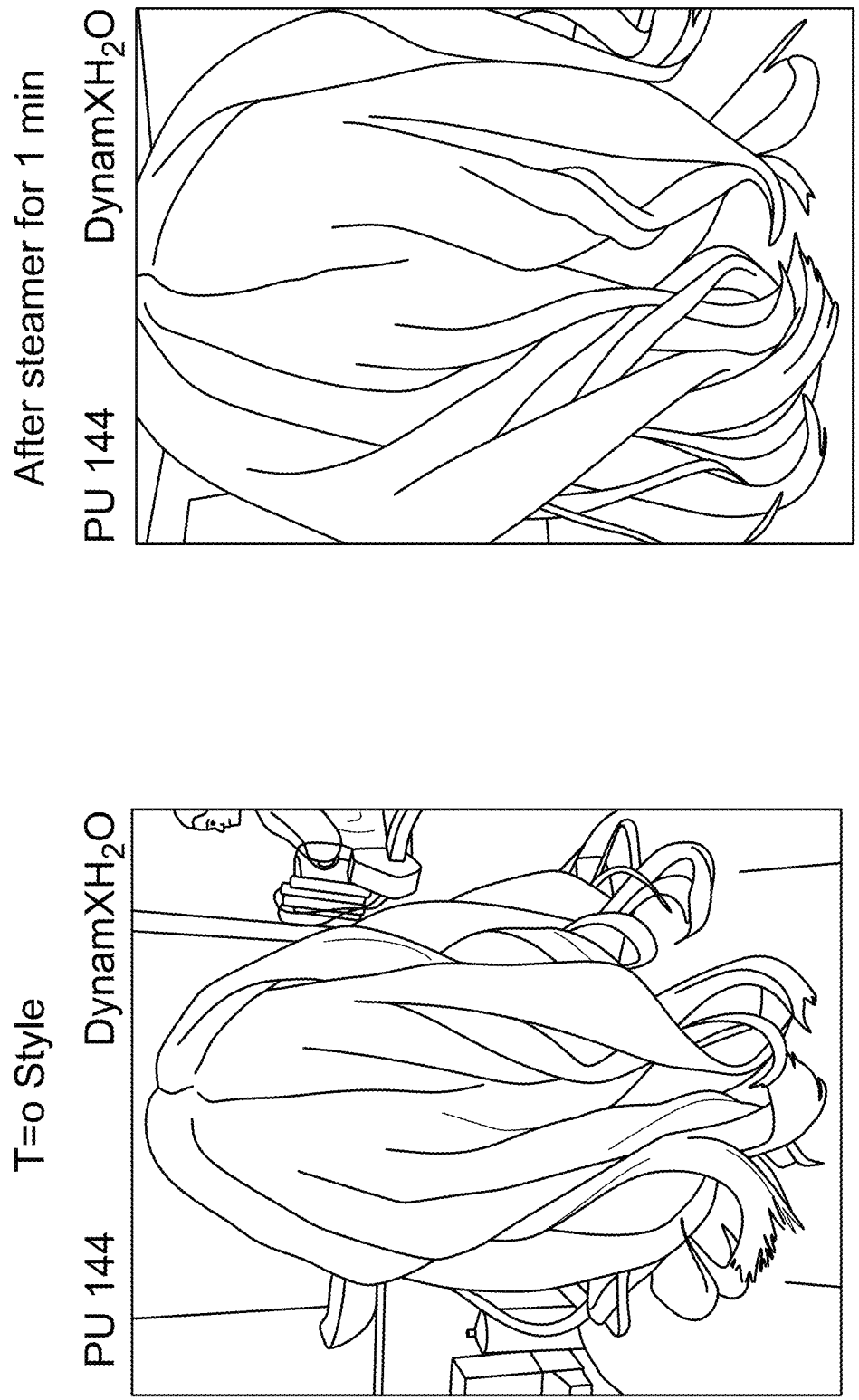
FIG. 6 is a set of photographs of a subject on which compositions were tested. In vivo curl retention of an inventive WBPU-U is compared with commercial WBPU DynamX $H_2O$. Trained stylists assigned PU 144 favorable scores for natural feeling and curl shape during blinded testing, and the enhanced curl definition of PU 144 compared to DynamX $H_2O$ after exposure to steam for 1 minute is shown here (In vivo method).
Figure 7:
FIG. 7 is a photograph of a subject on which compositions were tested. An inventive polycarbonate-based WBPU-U (PU 162) and PVP/VA were applied to each half of the head to and styled in loose, relaxed curls. PU 162 retains curl shape than the commercial resin after three hours of normal wear under ambient humidity (In vivo method).

Performance of the disclosed composition as compared to commercial products with regard to curl hold was tested using several different methods, including controlled mechanical stresses, humidity, sensory and in vivo salon testing. A summary of the testing methods and their key attributes is listed in Table 2. Furthermore, representative data is provided for Method VY-M (FIG. 2), Method VY-H (FIG. 3), Method VY-HB (FIG. 4), Method VY-S (FIG. 5), and in vivo methods (FIGS. 6 and 7).

TABLE 2

Figure 3:
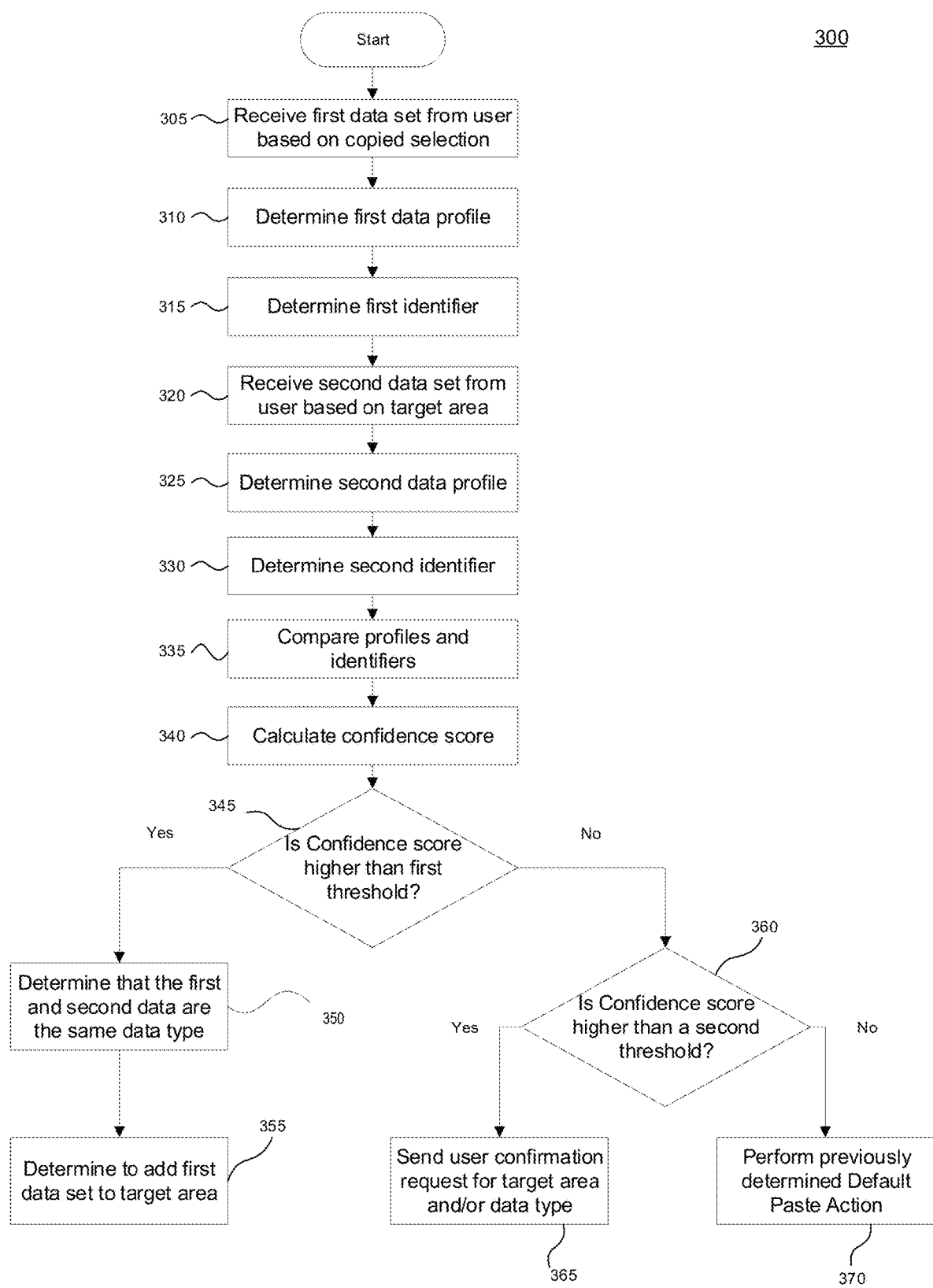
FIG. 3 is a table showing the increase in curl length at 90 minutes and 180 minutes under 75% relative humidity at 25° C. Inventive polycarbonate polyol-based WBPU-Us possessing the optimal properties (black) overall have minimal curl drop (Δ) when compared with suboptimal PCP-based WBPU-Us (crosshatched pattern), WBPU-Us based on other chemistries (diagonal pattern), and commercial resins (white). Curl drop Δ=(length of curled tress at 90 min or 180 min—length of tress at time 0)/(length of tress at time 0)*100 (Method VY-H).
Figure 4:
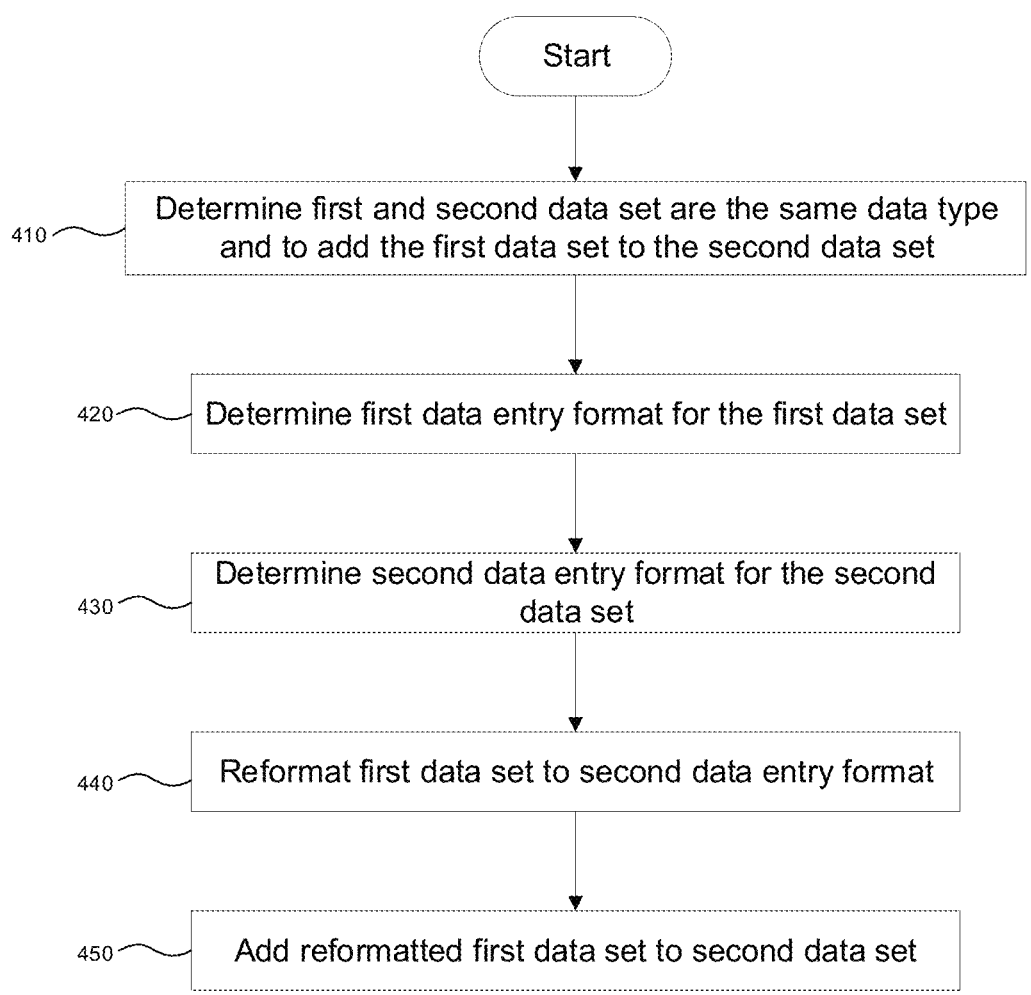
FIG. 4 is an image showing curl shape retention of two treated tresses after 32 hours under 75% relative humidity at 25° C. and subsequent brushing. The tress treated with the inventive polycarbonate-based PU 152 maintains excellent curl shape after significant humidity exposure and mechanical stress. It is shown in comparison to a tress treated with PVP/VA (Method VY-HB).

| Method | Preparation | Testing | Outcome |
| --- | --- | --- | --- |
| Method VY-M | Tress (resin dispersion applied) blow dried for 90 seconds, then curled using ¾" curling rod at 370° F. for 10 seconds and cooled in coiled formation. | Mechanically manipulated by pulling, separating, and brushing tresses in a controlled manner. Tress length recorded after each manipulation | Inventive polycarbonate-based WBPU-Us possessing the optimal mechanical properties and hydrophobicity have the least curl drop in response to a controlled pulling test. FIG. 2 |
| Method VY-H | Tress (resin dispersion applied) blow dried for 90 seconds, then curled using ¾" curling rod at 370° F. for 10 seconds and cooled in coiled formation. | Hung under 75% relative humidity at 25° C. Tress length recorded at various time points. | Inventive polycarbonate-based WBPUs possessing the optimal mechanical properties and hydrophobicity overall have minimal curl drop (Δ) when compared with suboptimal PCP-based WBPU-Us, non-PCP based WBPU-Us, and commercial resins. FIG. 3 |
| Method VY-HB | Tress (resin dispersion applied) blow dried for 90 seconds, then curled using ¾" curling rod at 370° F. for 10 seconds and cooled in coiled formation. | Hung at 75% relative humidity at 25° C. for 32 hours. Brushed 10-15 times. | A tress treated with the inventive polycarbonate-based PU 152 maintains excellent curl shape after significant humidity exposure. It is compared to a tress treated with PVP/VA. FIG. 4 |
| Method VY-S | Tress (resin dispersion applied) blow dried for 90 seconds. Tresses are prepared in duplicate and blinded randomly. | Evaluated for natural feeling and overall sensory attributes on a scale of −2 to 2 by trained sensory analysts under blinded conditions. | Inventive polycarbonate-based WBPU-Us provide superior sensory qualities compared with WBPU-Us containing other soft segment chemistries and with commercial resins. FIG. 5 |

TABLE 2-continued

| Method | Preparation | Testing | Outcome |
|---|---|---|---|
| In vivo Method | Panelist head is separated into two sections and two different resins are tested under identical styling conditions; both resins and conditions are variable depending on project goals | Testing conditions include mechanical manipulations (finger combing, brushing) and humidity testing with steamer. | A tress treated with inventive polycarbonate-based resin PU 144 retains better curl hold and shape than a tress treated with commercial resin DynamX H₂O after exposure to 1 minute of steam testing. FIG. 6 A tress treated with inventive polycarbonate-based resin PU 162 retains better curl hold and shape than a tress treated with commercial resin PVP/VA 635 after three hours of normal wear under ambient humidity FIG. 7 |

Example 5

Method VY-HM

A virgin brown tress (1.5 g) is coated with 800 μL of 3% resin dispersion, followed by blow drying for 90 seconds. The tress is combed once with a medium tooth comb and once with a fine-tooth comb after drying. The tress is curled at 370° F. for 10 seconds with a 1" diameter curling iron, and then cooled.

The initial curl length is measured, and then tress performance is measured by suspending the tress at 75% relative humidity at 25° C. for 15 minutes. The curl length is again measured. The tress is then combed once at a consistent rate with a medium-toothed comb and measured again.

Example 6

Method VY-MPull

A virgin brown tress (1.5 g) is coated with 800 μL of 3% resin dispersion, followed by blow drying for 90 seconds. The tress is combed once with a medium tooth comb and once with a fine-tooth comb at a consistent rate after drying. The tress is curled at 370° F. for 10 seconds with a 1" diameter curling iron, and then cooled.

The initial curl length is measured, and then tress performance is measured by a controlled pulling process. Two binder clips are suspended from the end of the tress for 10 seconds and then removed before re-measuring the curl length. This mechanical stress test is repeated twice more.

Example 7

Method VY-SP

A virgin brown tress (1.5 g) is coated with 800 μL of 3% resin dispersion, followed by blow drying for 90 seconds. The tress is combed once with a medium tooth comb and once with a fine-tooth comb after drying. The tress is curled at 370° F. for 10 seconds with a 1" diameter curling iron, and then cooled.

The initial curl length is measured, and then tress performance is measured by a water resistance test. Water is dispensed from a pump spray onto the tress three times 6" away from the tress, and then the curl is pulled to its full extension at a consistent rate and released four times. The final curl length is then measured.

Example 7

Comparative Data

The following data shows that WBPUs comprising a Young's modulus of above 150 MPa, an elongation at break from about 15% to about 300%, and moisture uptake of less than 10% for WBPUs without the addition of lipid and below 8% for WBPUs with lipid affords improved sensory and humidity performance Table 3 is a comparison of the chemical properties and ingredients of both exemplary and commercial WBPU-U compositions. The compositions are grouped by those which comprise a Young's modulus, an elongation at break, and moisture uptake defined herein. The actual values for these compositions are shown in Table 4.

TABLE 3

Exemplary and Commercial WBPU-U Compositions

| PU Name | NCO | Polyol (molar ratio to NCO) | Other diol segment (molar ratio to NCO) | Ionic chain extender (molar ratio to NCO) | Nonionic chain extender (molar ratio to NCO) | Neut. | Lipid |
|---|---|---|---|---|---|---|---|
| Exemplary WBPUs inside Selection Marker Ranges[1] | | | | | | | |
| 140 | IPDI | PCP/PEP2k_0.16 | N/A | DMBA_0.25 | L-Lysine_0.37 | $Na_2CO_3$ | N/A |
| 143 | IPDI | PCP/PEP2k_0.26 | N/A | DMBA_0.31 | L-Lysine_0.43 | $Na_2CO_3$ | N/A |
| 150 | IPDI | PCP1k_0.45 | N/A | DMBA_0.28 | L-Lysine_0.27 | $Na_2CO_3$ | OFPMA |
| 152 | IPDI | PCP1k_0.45 | N/A | DMBA_0.28 | L-Lysine_0.27 | $Na_2CO_3$ | N/A |
| 162 | IPDI | PCP1k_0.3 | BD_0.28 | DMBA_0.23 | L-Lysine_0.19 | $Na_2CO_3$ | N/A |
| 189 | IPDI | PCP1k_0.3 | BD_0.28 | DMBA_0.23 | L-Lysine_0.19 | $Na_2CO_3$ | OFPMA |

TABLE 3-continued

Exemplary and Commercial WBPU-U Compositions

| PU Name | NCO | Polyol (molar ratio to NCO) | Other diol segment (molar ratio to NCO) | Ionic chain extender (molar ratio to NCO) | Nonionic chain extender (molar ratio to NCO) | Neut. | Lipid |
|---|---|---|---|---|---|---|---|
| 235 | IPDI | PCP1k_0.3 | BD_0.28 | DMBA_0.23 | L-Lysine_0.19 | $Na_2CO_3$ | Ionone |
| 249 | IPDI | PCP1k_0.3 | BD_0.28 | DMBA_0.23 | L-Lysine_0.19 | $Na_2CO_3$ | Ionone |
| 281 | IPDI | PCP1k_0.3 | BD_0.28 | DMBA_0.23 | L-Lysine_0.19 | $Na_2CO_3$ | N/A |
| 299 | IPDI | PCP1k_0.3 | BD_0.28 | DMBA_0.23 | L-Lysine_0.19 | $Na_2CO_3$ | Oleic acid |
| WBPUs Outside Selection Marker Ranges[2] | | | | | | | |
| 103 | IPDI | PEtP1k_0.34 | N/A | DMBA_0.30 | L-Lysine_0.37 | $Na_2CO_3$ | N/A |
| 172 | IPDI | PEtP1k_0.32 | BD_0.34 | DMAPD_0.35 | N/A | Lactic acid | N/A |
| 191 | IPDI | PCP1k_0.25 | HD_0.21 | DMBA_0.22 | L-Lysine_0.33 | $Na_2CO_3$ | N/A |
| 192 | IPDI | PCP1k_0.25 | HD_0.21 | DMBA_0.22 | L-Lysine_0.33 | $Na_2CO_3$ | OFPMA |
| 291 | IPDI | PEtP1k_0.35 | N/A | DMBA_0.30 | L-Lysine_0.35 | $Na_2CO_3$ | Ionone |
| Baycusan C1004 | | | Commercial | | | | N/A |
| Baycusan C1008 | | | Commercial | | | | N/A |
| DynamX $H_2O$ | | | Commercial | | | | N/A |
| Polyderm PE/PAED | | | Commercial | | | | N/A |
| Luviset PUR | | | Commercial | | | | N/A |

[1]Exemplary WBPUs comprise a Young's modulus >150 MPa, an elongation at break between 15% and 300%, and water uptake below 10% for WBPUs without the addition of lipid and below 8% for WBPUs with lipid (OFPMA, Oleic acid, or Ionone).
[2]WBPUs outside of the disclosed Young's modulus, elongation at break, and moisture uptake.

TABLE 4

Mechanical properties and water uptake of example WBPU-Us

| PU Name | Young's modulus (MPa) | Elong. at break (%) | $H_2O$ uptake (%) |
|---|---|---|---|
| Inside Disclosed Selection Marker Range | | | |
| 140 | 428 ± 7 | 233 ± 0 | 6.76 ± 0.05 |
| 143 | 291 ± 15 | 183 ± 35 | 7.58 ± 0.11 |
| 150 | 123 ± 17 | 276 ± 85 | 2.58 ± 0.16 |
| 152 | 174 ± 12 | 182 ± 37 | 6.94 ± 0.13 |
| 162 | 381 ± 14 | 103 ± 15 | 6.75 ± 0.09 |
| 189 | 296 ± 21 | 20 ± 6 | 4.03 ± 0.17 |
| 235 | 109 ± 4 | 146 ± 28 | 3.48 ± 0.14 |
| 249 | 187 ± 12 | 208 ± 27 | 5.38 ± 0.06 |
| 299 | 332 ± 20 | 145 ± 28 | 6.74 ± 0.21 |
| Outside Disclosed Selection Marker Range | | | |
| 103 | 214 ± 18 | 160 ± 19 | 10.10 ± 0.10 |
| 172 | 112 ± 11 | 176 ± 25 | 7.75 ± 0.08 |
| 191 | 361 ± 48 | 10 ± 2 | 8.40 ± 0.10 |
| 192 | 353 ± 21 | 8 ± 2 | 6.30 ± 0.30 |
| 291 | 209 ± 11 | 172 ± 89 | 9.34 ± 0.05 |
| Baycusan C1004 | 14 ± 0 | 406 ± 18 | 2.90 ± 0.11 |
| Baycusan C1008 | 3 ± 0 | >1,000 | 3.30 ± 0.04 |
| DynamX $H_2O$ | 447 ± 14 | 7 ± 1 | 904 |
| Polyderm PE/PA ED | 38 ± 2 | 514 ± 2 | 5.22 ± 0.07 |
| Luviset PUR | Too brittle to measure | Too brittle to measure | 5.63 ± 0.31 |

Unique and superior morphology was also found with the inventive compositions. For example, transmission electron microscopy (TEM) images revealed that the addition of the disclosed lipids (e.g., oil) as shown in FIG. 12 Panel B led to a morphology that is unique from the morphology of WBPU alone (FIG. 12, Panel A) and a simple blend of the WBPU and lipid (FIG. 12, Panel C). In addition, when compared with commercially available compositions, optimal particle size and morphology was obtained. See e.g., FIG. 13, where TEM analyses shows that PU 281, having a Young's modulus: 315 MPa, an elongation at break: 47%, and a water uptake: 5.95% consists of well dispersed spherical particles with primary size of 27±4 nm. See FIG. 13 Panel A and B. Commercially available WBPUs, however, contain either highly cross-linked aggregates (See FIG. 13 Panel C and D, DynamX $H_2O$) or much larger particles (See FIG. 13 Panel E and F, C1010, average size: 159±51 nm). All analyses were performed on a JEOL JEM-1010 instrument with an accelerating voltage of 80 kV. Samples were stained with 2% uranyl acetate to enhance the contrast.

Figure 14:
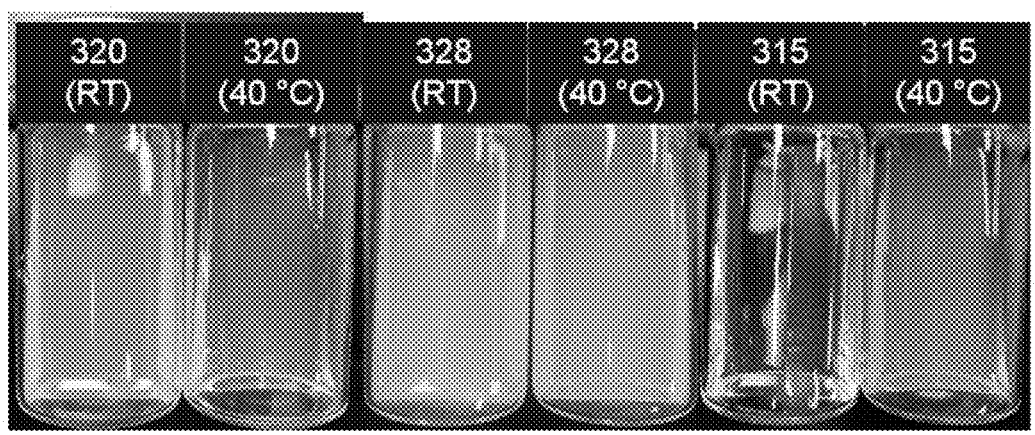
FIG. 14. illustrates that WBPUs having the disclosed properties were stable at 40° C. for 12 weeks (accelerated aging conditions), which translates to 2-year shelf life at room temperature.

In addition to particle properties, enhanced stability was also observed with the inventive compositions. For example, dispersion testing revealed that the disclosed WBPUs were stable at 40° C. for 12 weeks (accelerated aging conditions). See e.g., FIG. 14. This translates to 3-year shelf life at room temperature. The pictures in FIG. 14 show that the optimal inventive WBPUs remained similar viscosity as the room temperature controls. (All the sample vials were tilted to show the dispersion flow; the optimal inventive WBPUs both at RT and at 40° C. flow upon tilting). PU 320: (1) Young's modulus: 343±59 MPa, (2) Elongation at break: 16±3%, (3) Water uptake: 6.52±0.14%, and (4) Particle size: 38.6±10.2 nm with desired morphology for WBPU dispersion stability (mainly spheres). PU 328: (1) Young's modulus: 359±20 MPa, (2) Elongation at break: 85±25%, (3) Water uptake: 6.02±0.26%, and (4) Particle size: 31.6±16.3 nm with desired morphology for WBPU dispersion stability (mainly spheres and minimal chains). PU 315: (1) Young's modulus: 374±41 MPa, (2) Elongation at break: 45±16%, (3) Water uptake: 7.63±0.14%, and (4) Particle size: 27.1±2.9 nm with desired morphology for WBPU dispersion stability (mainly spheres and minimal chains).

Figure 15:
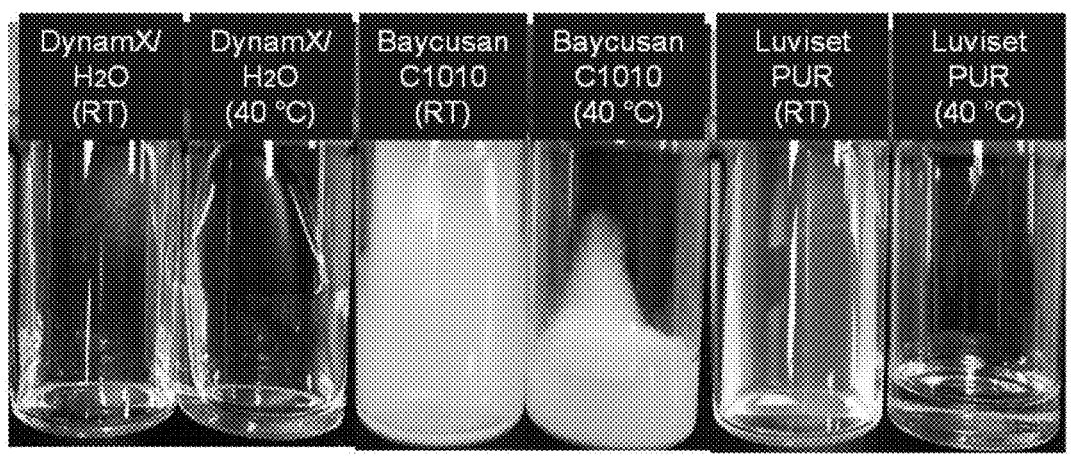
FIG. 15 illustrates that compositions not having the disclosed properties are unstable at 40° C.

In the same study, commercial WBPUs having suboptimal properties (Table 2) were unstable at 40° C. See FIG. 15. The pictures demonstrate that DynamX/$H_2O$ turned into thicker dispersion at 40° C. for 4 weeks; Baycusan C1010 and Luviset PUR both gelled up at 40° C. for 12 weeks (All the sample vials were tilted to show the dispersion flow; Baycusan C1010 and Luviset PUR dispersions at 40° C. do not flow). Baycusan C1010: suboptimal properties (1) Young's modulus: 87±3 MPa, (2) Elongation at break: 86±12%, (3) Water uptake: 2.62±0.03%, and (4) Particle size: 159.3±50.6 nm with undesired morphology for WBPU dispersion stability (large spheres).

Sensory and humidity performance testing was also performed and the data is shown in Tables 5 and 6. Compositions comprising WBPUs within the disclosed selection marker range significantly outperformed comparator composition in one or both measures. Average sensory scores were determined according to Method VY-S. For each resin, sample size 5≤N≤32. Humidity measurements were determined according to Method VY-H. For each resin, sample size 3≤N≤11.

TABLE 5

Sensory evaluation data of selected LP WBPU-Us

| PU Name | Average Sensory Score[1] |
|---|---|
| Inside Disclosed Selection Marker Range | |
| 140 | 0.20 |
| 150 | 0.32 |
| 152 | 0.62 |
| 162 | 0.06 |
| 235 | 0.36 |
| 249 | 1.27 |
| 299 | 1.12 |
| Outside Disclosed Selection Marker Range | |
| 103 | −0.23 |
| 172 | 0.41 |
| 191 | −0.21 |
| 291 | −0.03 |
| C1004 | −0.44 |
| C1008 | −0.85 |
| DynamX/$H_2O$ | 0.14 |
| Polyderm PE/PA ED | −1.31 |

TABLE 6

Humidity performance data of selected LP WBPU-Us

| PU Name | Average % Curl Drop after 30 Minutes[1] |
|---|---|
| Inside Disclosed Selection Marker Range | |
| 140 | 51.2 |
| 143 | 90.2 |
| 152 | 49.2 |
| 162 | 67.2 |
| 189 | 55.8 |
| 249 | 75.9 |

TABLE 6-continued

Humidity performance data of selected LP WBPU-Us

| PU Name | Average % Curl Drop after 30 Minutes[1] |
|---|---|
| Outside Disclosed Selection Marker Range | |
| 103 | 83.4 |
| 172 | 88.9 |
| 192 | 82.3 |
| 201 | 82.8 |
| C1004 | 87.8 |
| C1008 | 69.7 |
| DynamX/$H_2O$ | 131.7 |
| Poly derm PE/PA ED | 104.8 |
| Luviset PUR | 71.1 |

Figure 8:
FIG. 8 is a photograph of a mannequin showing excellent initial curl shape and definition from LP PU 299 before (left image) and after (right image) controlled high humidity conditions.
Figure 9:
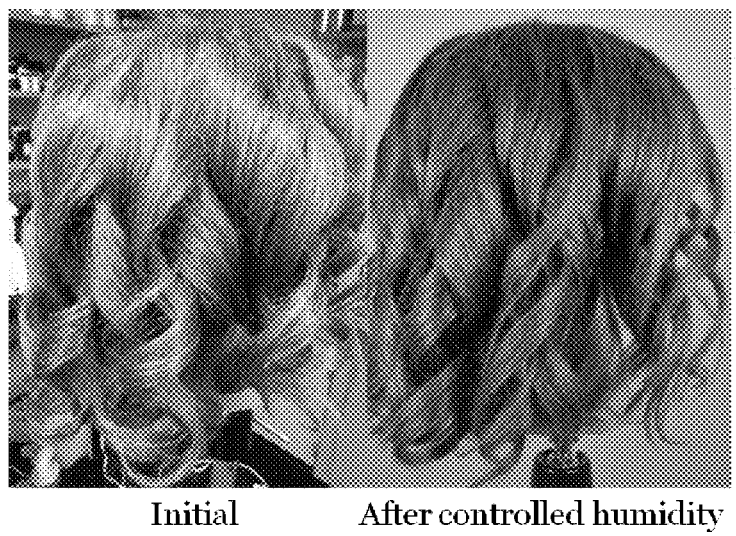
FIG. 9 is a photograph of a commercial composition WBPU DynamX $H_2O$ having properties outside of the disclosed selection markers, where poor curl shape and definition was observed before (left image) and after (right image) controlled high humidity conditions.

Similar trends are also shown by FIGS. 8-11. For example, when applied to the hair, excellent initial curl shape and definition was observed using exemplary composition PU 299 (left image). See FIG. 8. The right image in FIG. 8 shows the excellent retention of curl shape and definition after high humidity conditions. Hair styling professionals reported that hair treated and styled with LP PU 299 is soft and natural-feeling, with pleasing curl shape. Overall, WBPU-Us with selection markers of the disclosed ranges have similar results. The commercial composition, WBPU DynamX $H_2O$, does not have the same favorable results. See e.g., FIG. 9. WBPU DynamX $H_2O$, does not have features falling within each of the disclosed selection markers and exhibits poor initial curl shape and definition. See FIG. 9, left image. It also shows poor retention of curl shape and definition after high humidity conditions. See FIG. 9, right image. Hair styling professionals reported that hair treated and styled with LP DynamX $H_2O$ is crunchy feeling, and has unfavorable curl shape.

Figure 10:
FIG. 10 is a photograph of a subject on which an exemplary composition was tested. Excellent initial curl shape and definition was seen before (left image) and after (right image) controlled high humidity conditions (in vivo method).
Figure 11:
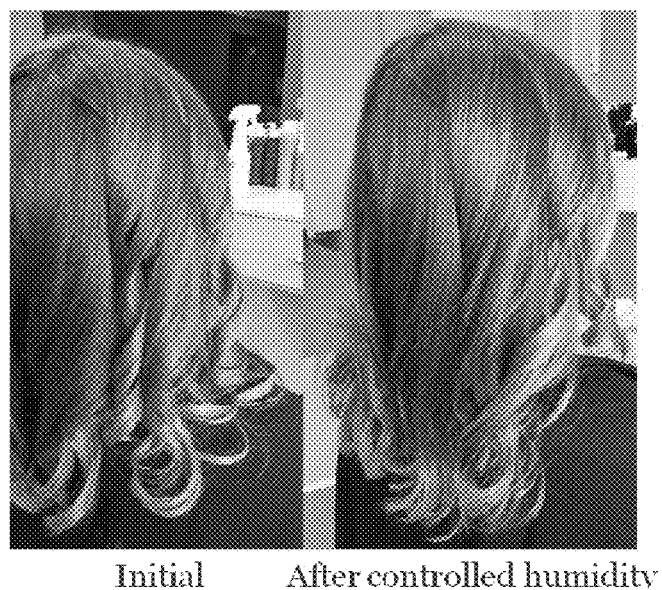
FIG. 11 is a photograph of a subject on which a commercial composition was tested. Poor curl shape and definition was observed before (left image) and after (right image) controlled high humidity conditions (in vivo method).

A direct in vivo comparison was also performed using PU 299 and commercially available WBPU DynamX $H_2O$. See FIGS. 10 and 11. The left image in FIG. 10 shows the excellent initial curl shape and definition of the optimal PU 299. In contrast, the left image in FIG. 11 shows that WBPU DynamX $H_2O$ has poor initial curl shape and definition. The right image FIG. 10 shows the excellent retention of curl shape and definition after high humidity conditions. In contrast, the right image in FIG. 11 shows that WBPU DynamX $H_2O$ has poor retention of curl shape and definition after high humidity conditions. Measurements were determined according to Method VY-MQ and in the in vivo methods as described herein.

The invention claimed is:

1. A composition comprising a polyurethane-urea formed from a soft segment and a hard segment, wherein the soft segment is formed from a polycarbonate polyol W; and the hard segment is formed from monomer units of X, Y, $Z^1$ and $Z^2$, wherein
    (i) X is isophorone diisocyanate (IPDI);
    Y is dimethylolbutyric acid (DMBA);
    $Z^1$ is butanediol (BD); and
    $Z^2$ is L-Lysine;
    wherein
    (a) the molecular weight of W is 1,000 g/mol;
    the molar ratio of X:W is 1:0.3, 1:0.32, 1:0.34, 1:0.43, or 1:0.45;
    the molar ratio of X:Y is 1:0.23, 1:0.24, 1:0.27, or 1:0.28;
    the molar ratio of X:$Z^1$ is 1:0, 1:0.04, 1:0.1, or 1:0.13; and the molar ratio of X:Z² is 1:0.06, 1:0.19, 1:0.27, 1:0.29, 1:0.36, or 1:0.44, and
wherein the polyurethane-urea is neutralized with $Na_2CO_3$ or triethylamine (TEA); or
(b) the molecular weight of W is 2,000 g/mol;
the molar ratio of X:W is 1:0.24;
the molar ratio of X:Y is 1:0.31;
the molar ratio of X:Z¹ is 1:0; and
the molar ratio of X:Z² is 1:0.45, and
wherein the polyurethane-urea is neutralized with $Na_2CO_3$;
(ii) X is isophorone diisocyanate (IPDI);
Y is dimethylolbutyric acid (DMBA);
Z¹ is hexanediol (HD); and
Z² is L-Lysine;
wherein
(a) the molecular weight of W is 1,000 g/mol;
the molar ratio of X:W is 1:0.25;
the molar ratio of X:Y is 1:0.22;
the molar ratio of X:Z¹ is 1:0.11; and
the molar ratio of X:Z² is 1:0.21, and
wherein the polyurethane-urea is neutralized with $Na_2CO_3$; or
(b) the molecular weight of W is 2,000 g/mol;
the molar ratio of X:W is 1:0.07;
the molar ratio of X:Y is 1:0.18;
the molar ratio of X:Z¹ is 1:0.26; and
the molar ratio of X:Z² is 1:0.25, and
wherein the polyurethane-urea is neutralized with $Na_2CO_3$;
(iii) X is isophorone diisocyanate (IPDI);
Y is 3-dimethylamino-1,2-propanediol (DMAPD);
Z¹ is butanediol (BD); and
Z² is L-Lysine;
wherein
the molecular weight of W is 1,000 g/mol;
the molar ratio of X:W is 1:0.27 or 1:0.42;
the molar ratio of X:Y is 1:0.27 or 1:0.33;
the molar ratio of X:Z¹ is 1:0.1 or 1:0.18; and
the molar ratio of X:Z² is 1:0, and
wherein the polyurethane-urea is neutralized with lactic acid; or
(iv) X is bis-(4-isocyanatocyclohexyl)-methane ($H_{12}MDI$);
Y is dimethylolbutyric acid (DMBA);
Z¹ is butanediol (BD); and
Z² is L-Lysine;
wherein
the molecular weight of W is 1,000 g/mol;
the molar ratio of X:W is 1:0.34;
the molar ratio of X:Y is 1:0.25;
the molar ratio of X:Z1 is 1:0.04; and
the molar ratio of X:Z2 is 1:0.11, and
wherein the polyurethane-urea is neutralized with lactic acid; and
wherein the Young's modulus of the polyurethane-urea is above 150 MPa; the elongation at break of the polyurethane-urea is from about 15% to about 300%; and the moisture uptake of the polyurethane-urea is less than 10%;
wherein the polyurethane-urea is selected such that the composition, after being applied to a curled hair tress and dried thereon, provides less than 80% change in tress length as measured by the high humidity mechanical stress test; and
wherein the soft segment, hard segment, and chain extender do not comprise isophorone diamine (IPDA).

2. A composition comprising a polyurethane-urea formed from a soft segment and a hard segment, wherein the soft segment is formed from a polycarbonate polyol W; and the hard segment is formed from monomer units of X, Y, Z¹ and Z², wherein
(i) X is isophorone diisocyanate (IPDI);
Y is dimethylolbutyric acid (DMBA);
Z¹ is butanediol (BD); and
Z² is L-Lysine;
wherein
(a) the molecular weight of W is 1,000 g/mol;
the molar ratio of X:W is 1:0.3, 1:0.32, 1:0.34, 1:0.43, or 1:0.45;
the molar ratio of X:Y is 1:0.23, 1:0.24, 1:0.27, or 1:0.28;
the molar ratio of X:Z1 is 1:0, 1:0.04, 1:0.1, or 1:0.13; and
the molar ratio of X:Z2 is 1:0.06, 1:0.19, 1:0.27, 1:0.29, 1:0.36, or 1:0.44, and
wherein the polyurethane-urea is neutralized with $Na_2CO_3$ or triethylamine (TEA); or
(b) the molecular weight of W is 2,000 g/mol;
the molar ratio of X:W is 1:0.24;
the molar ratio of X:Y is 1:0.31;
the molar ratio of X:Z1 is 1:0; and
the molar ratio of X:Z2 is 1:0.45, and
wherein the polyurethane-urea is neutralized with $Na_2CO_3$;
(ii) X is isophorone diisocyanate (IPDI);
Y is dimethylolbutyric acid (DMBA);
Z¹ is hexanediol (HD); and
Z² is L-Lysine;
wherein
(a) the molecular weight of W is 1,000 g/mol;
the molar ratio of X:W is 1:0.25;
the molar ratio of X:Y is 1:0.22;
the molar ratio of X:Z1 is 1:0.11; and
the molar ratio of X:Z2 is 1:0.21, and
wherein the polyurethane-urea is neutralized with $Na_2CO_3$; or
(b) the molecular weight of W is 2,000 g/mol;
the molar ratio of X:W is 1:0.07;
the molar ratio of X:Y is 1:0.18;
the molar ratio of X:Z1 is 1:0.26; and
the molar ratio of X:Z2 is 1:0.25, and
wherein the polyurethane-urea is neutralized with Na2CO3;
(iii) X is isophorone diisocyanate (IPDI);
Y is 3-dimethylamino-1,2-propanediol (DMAPD);
Z¹ is butanediol (BD); and
Z² is L-Lysine;
wherein
the molecular weight of W is 1,000 g/mol;
the molar ratio of X:W is 1:0.27 or 1:0.42;
the molar ratio of X:Y is 1:0.27 or 1:0.33;
the molar ratio of X:Z1 is 1:0.1 or 1:0.18; and
the molar ratio of X:Z2 is 1:0, and
wherein the polyurethane-urea is neutralized with lactic acid; or
(iv) X is bis-(4-isocyanatocyclohexyl)-methane ($H_{12}MDI$);
Y is dimethylolbutyric acid (DMBA);
Z¹ is butanediol (BD); and
Z² is L-Lysine;
wherein
the molecular weight of W is 1,000 g/mol;
the molar ratio of X:W is 1:0.34:
the molar ratio of X:Y is 1:0.25;

the molar ratio of X:Z1 is 1:0.04; and
the molar ratio of X:Z2 is 1:0.11, and wherein the polyurethane-urea is neutralized with lactic acid; and
wherein the Young's modulus of the polyurethane-urea is above 150 MPa; the elongation at break of the polyurethane-urea is from about 15% to about 300%; and the moisture uptake of the polyurethane-urea is less than 10%;
wherein the polyurethane-urea is selected such that the composition, after being applied to a hair tress and dried thereon, provides a sensory score of at least 0; and
wherein the soft segment, hard segment, and chain extender do not comprise isophorone diamine (IPDA).

3. A composition comprising a polyurethane-urea formed from a soft segment and a hard segment, wherein the soft segment is formed from a polycarbonate polyol W;
and the hard segment is formed from monomer units of X, Y, $Z^1$ and $Z^2$, wherein
(i) X is isophorone diisocyanate (IPDI);
Y is dimethylolbutyric acid (DMBA);
$Z^1$ is butanediol (BD); and
$Z^2$ is L-Lysine;
wherein
(a) the molecular weight of W is 1,000 g/mol;
the molar ratio of X:W is 1:0.3, 1:0.32, 1:0.34, 1:0.43, or 1:0.45;
the molar ratio of X:Y is 1:0.23, 1:0.24, 1:0.27, or 1:0.28;
the molar ratio of X:$Z^1$ is 1:0, 1:0.04, 1:0.1, or 1:0.13; and
the molar ratio of X:$Z^2$ is 1:0.06, 1:0.19, 1:0.27, 1:0.29, 1:0.36, or 1:0.44, and
wherein the polyurethane-urea is neutralized with $Na_2CO_3$ or triethylamine (TEA); or
(b) the molecular weight of W is 2,000 g/mol;
the molar ratio of X:W is 1:0.24;
the molar ratio of X:Y is 1:0.31;
the molar ratio of X:Z1 is 1:0; and
the molar ratio of X:Z2 is 1:0.45, and
wherein the polyurethane-urea is neutralized with $Na_2CO_3$;
(ii) X is isophorone diisocyanate (IPDI);
Y is dimethylolbutyric acid (DMBA);
$Z^1$ is hexanediol (HD); and
$Z^2$ is L-Lysine;
wherein
(a) the molecular weight of W is 1,000 g/mol;
the molar ratio of X:W is 1:0.25;
the molar ratio of X:Y is 1:0.22;
the molar ratio of X:Z1 is 1:0.11; and
the molar ratio of X:Z2 is 1:0.21, and
wherein the polyurethane-urea is neutralized with $Na_2CO_3$; or
(b) the molecular weight of W is 2,000 g/mol;
the molar ratio of X:W is 1:0.07;
the molar ratio of X:Y is 1:0.18;
the molar ratio of X:Z1 is 1:0.26; and
the molar ratio of X:Z2 is 1:0.25, and
wherein the polyurethane-urea is neutralized with $Na_2CO_3$;
(iii) X is isophorone diisocyanate (IPDI);
Y is 3-dimethylamino-1,2-propanediol (DMAPD);
$Z^1$ is butanediol (BD); and
$Z^2$ is L-Lysine;
wherein
the molecular weight of W is 1,000 g/mol;
the molar ratio of X:W is 1:0.27 or 1:0.42;
the molar ratio of X:Y is 1:0.27 or 1:0.33;
the molar ratio of X:Z1 is 1:0.1 or 1:0.18; and
the molar ratio of X:Z2 is 1:0, and
wherein the polyurethane-urea is neutralized with lactic acid; or
(iv) X is bis-(4-isocyanatocyclohexyl)-methane ($H_{12}MDI$);
Y is dimethylolbutyric acid (DMBA);
$Z^1$ is butanediol (BD); and
$Z^2$ is L-Lysine;
wherein
the molecular weight of W is 1,000 g/mol;
the molar ratio of X:W is 1:0.34;
the molar ratio of X:Y is 1:0.25;
the molar ratio of X:Z1 is 1:0.04; and
the molar ratio of X:Z2 is 1:0.11, and
wherein the polyurethane-urea is neutralized with lactic acid; and
wherein the Young's modulus of the polyurethane-urea is above 150 MPa; the elongation at break of the polyurethane-urea is from about 15% to about 300%; and the moisture uptake of the polyurethane-urea is less than 10%;
wherein the polyurethane-urea is dispersed in water to form a polyurethane-urea particle with a particle size of less than 200 nm; and wherein the moisture uptake of the polyurethane-urea is less than 10%; and
wherein the soft segment, hard segment, and chain extender do not comprise isophorone diamine (IPDA).

4. The composition of claim 1, wherein the composition further comprises a performance-enhancing lipid; wherein the performance-enhancing lipid is associated with polyurethane-urea to form a polyurethane-urea:performance-enhancing lipid complex and wherein the polyurethane-urea: performance-enhancing lipid complex is dispersed in water.

5. The composition of claim 1, wherein the polyurethane-urea is dispersed in an aqueous solution.

6. The composition of claim 1, wherein
the Young's modulus of the polyurethane-urea polymer is from about 150 MPa to about 500 Mpa; and
the moisture uptake of the polyurethane-urea is from about 0% to about 10%.

7. The composition of claim 1, wherein the polyurethane-urea is dispersed in water to form a polyurethane-urea particle with a particle size of less than 200 nm; and
wherein the moisture uptake of the polyurethane-urea is less than 8%.

8. The composition of claim 1, wherein the polyurethane-urea is selected such that the polyurethane-urea dispersed in water forms a polyurethane-urea particle with a particle size of less than 40 nm.

9. The composition of claim 2, wherein the polyurethane-urea is selected such that the polyurethane-urea dispersed in water forms a polyurethane-urea particle with a particle size of less than 40 nm.

10. The composition of claim 3, wherein the polyurethane-urea dispersed in water forms a polyurethane-urea particle with a particle size of less than 40 nm.

11. The composition of claim 1, wherein the polyurethane-urea further comprises an additive selected from 2,2,3,3,4,4,5,5-octafluoropentyl methacrylate (OFPMA), squalene, or ionone.

12. The composition of claim 2, wherein the polyurethane-urea further comprises an additive selected from 2,2,3,3,4,4,5,5-octafluoropentyl methacrylate (OFPMA), squalene, or ionone.

13. The composition of claim 3, wherein the polyurethane-urea further comprises an additive selected from 2,2,3,3,4,4,5,5-octafluoropentyl methacrylate (OFPMA), squalene, or ionone.

* * * * *